(12) United States Patent
Yang

(10) Patent No.: US 7,070,965 B1
(45) Date of Patent: Jul. 4, 2006

(54) SMALL MOLECULE ANTICANCER COMPOUNDS AND RELATED PRODUCTION PROCESS

(76) Inventor: Zhenhua Yang, 3008 Andalucia Dr., West Covina, CA (US) 91791

( * ) Notice: Subject to any disclaimer, the term of this patent is extended or adjusted under 35 U.S.C. 154(b) by 0 days.

(21) Appl. No.: 09/647,918

(22) PCT Filed: Apr. 14, 1999

(86) PCT No.: PCT/US99/06525

§ 371 (c)(1),
(2), (4) Date: Mar. 8, 2001

(87) PCT Pub. No.: WO99/53086

PCT Pub. Date: Oct. 21, 1999

Related U.S. Application Data

(63) Continuation-in-part of application No. 09/173,681, filed on Oct. 16, 1998, now Pat. No. 6,214,875.

(60) Provisional application No. 60/081,712, filed on Apr. 14, 1998.

(51) Int. Cl.
*C12P 7/64* (2006.01)

(52) U.S. Cl. ...................... 435/134; 435/132; 435/155; 424/115; 424/451; 424/780; 514/557; 514/558

(58) Field of Classification Search ............. 435/243.1, 435/41, 134, 132, 155; 424/451, 115, 780; 514/557, 558
See application file for complete search history.

(56) References Cited

U.S. PATENT DOCUMENTS

| | | | |
|---|---|---|---|
| 4,985,466 A | | 1/1991 | Deguchi et al. |
| 5,854,280 A | * | 12/1998 | Gomez et al. |
| 6,214,875 B1 | * | 4/2001 | Yang |

FOREIGN PATENT DOCUMENTS

| CA | 2020633 | 1/1991 |
|---|---|---|
| EP | 0 332 001 A | 9/1989 |
| JP | 63 088123 A | 4/1988 |
| JP | 07 002661 A | 1/1995 |

OTHER PUBLICATIONS

Won-Bae Kang et al, "Chemotaxonomic Classification of Marine Bacteria on the Basis of Fatty Acid Compositions", Journal of Korean Fisheries Society, vol. 30, No. 6, Nov. 1997, pp. 1013-1020.

* cited by examiner

*Primary Examiner*—Leon B. Lankford, Jr.
(74) *Attorney, Agent, or Firm*—Oblon, Spivak, McClelland, Maier & Neustadt, P.C.

(57) ABSTRACT

A group of specific branched-chain fatty acids, with significant anticancer effects on human and animals; methods of making using either chemical synthesis or biosynthesis methods; and methods of treating cancer.

20 Claims, 10 Drawing Sheets

SCALE BAR
= 2 μM

SCALE BAR
= 2 μM

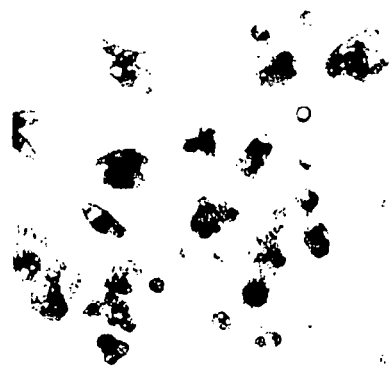
FIG.2A        FIG.2B
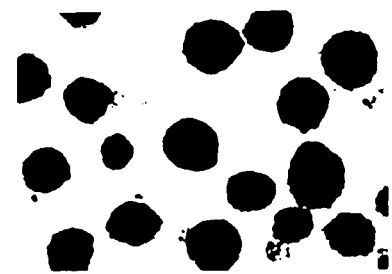
FIG.3A        FIG.3B
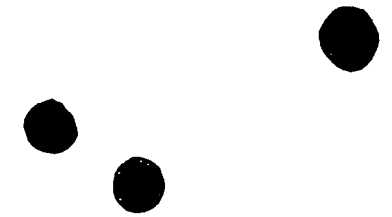
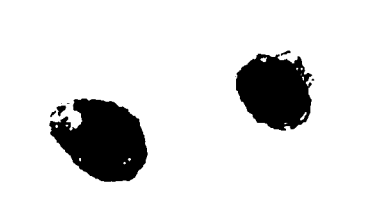
FIG.4A        FIG.4B

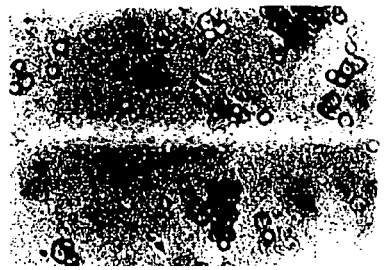
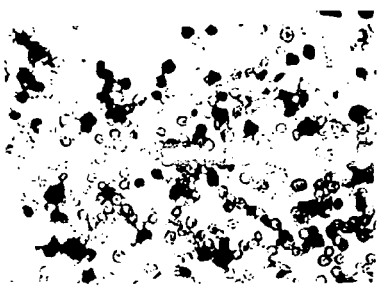
FIG.10A FIG.10B
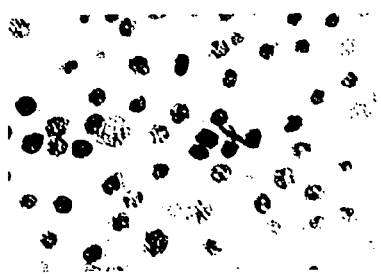
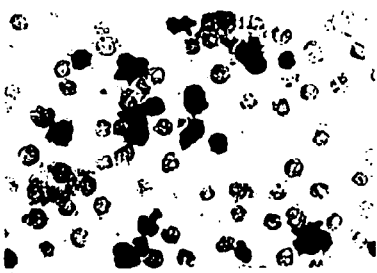
FIG.11A FIG.11B
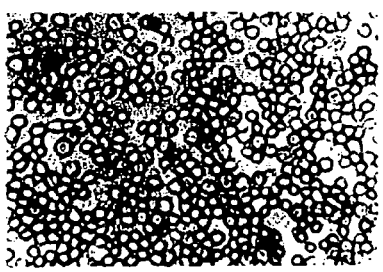
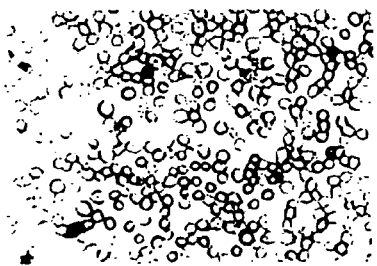
FIG.12A FIG.12B

SMALL MOLECULE ANTICANCER COMPOUNDS AND RELATED PRODUCTION PROCESS

This application is a continuation in part of U.S. application Ser. No. 09/173,681 filed Oct. 16, 1998, now U.S. Pat. No. 6,214,875, which application claims the benefit of U.S. Provisional Application 60/081,712, filed Apr. 14, 1998.

BACKGROUND OF THE INVENTION

1. Field of the Invention

The present invention relates to a group of compounds, i.e., specific branched-chain fatty acids, and pharmaceutically acceptable salts and derivatives thereof, with significant anticancer activities, and methods of treating cancer. The invention also relates to a process of producing fermentation products containing said specific branched-chain fatty acids, using specific bacteria strains, preferably in industrial facilities.

2. Description of the Background

Carcinoma is one of the most serious diseases threatening human's health and life. So far the predominant treatments to cancer patients are radiotherapy and chemotherapy. Both have certain toxicity or side effects on humans while suppressing cancer cell growth or killing cancer cells. Therefore extensive investigations have been carried out in order to find an effective anti-carcinogen with minimum side effects and toxicity.

In 1987, when the inventor cultured K562 leukemia cell lines in the laboratory, cells in a culture flask were found to have completely disappeared 48 hours after being contaminated by a kind of rod bacteria. Those rod bacteria were then intentionally harvested and purified, and incubated in soybean media with appropriate inorganic salts. It was found in later animal studies that the fermentation solution effectively inhibited tumor growth with no toxicity or side effects. In the decade since then, thousands of cancer patients, including advanced stage cancer patients, have been treated with the oral liquid developed from this fermentation solution. These include leukemia, tongue cancer, colorectal cancer, breast cancer, prostate cancer, lung cancer, gastric cancer, hepatocarcinoma, melanocarcinoma, renal cancer, esophagus cancer and pancreas cancer patients. Most of them have responded to the oral liquid, such as by symptom improvement, tumor shrinkage or even complete disappearance. Many of these patients are still alive today. The cases included patients in China, Japan, Korea, the United States, and many other countries.

In order to discover the active components in the fermentation solution that play a key role in killing cancer cells, persistent investigations have been carried out for the last ten years. In this period many books and papers were published worldwide trying to explain the anticancer activity of this fermentation solution. Most of these reports suggested that some soybean isoflavones (e.g. genistein, daidzein and saponin) from the soybean media contributed to the anticancer activities of this fermentation solution. On the other hand, some clinical trials indicated that the anticancer activities of soybean isoflavones were not great enough to explain the anticancer effects of the fermentation solution. The inventor has isolated many compounds from the fermentation solution and revealed that the anticancer activities of the solution were largely contributed by 13-methyltetradecanoic acid and 12-methyltetradecanoic acid. Further investigations discovered that other members of the family of branched-chain fatty acids also had significant tumor-inhibition effects. So far there are no other reports in the literature regarding the anticancer activity of specific branched-chain fatty acids.

SUMMARY OF THE INVENTION

The present invention relates to a group of compounds, i.e., specific branched-chain fatty acids, and pharmaceutically acceptable salts and derivatives thereof, with significant anticancer activities, and methods of treating cancer using these compounds. Comprehensive biochemical and morphological tests have demonstrated that these activities are associated with induction of programmed cancer cell death (apoptosis). Very importantly, the specific branched-chain fatty acids do not kill normal cells. In animal studies, intraperitoneal injection of 13-methyltetradecanoic acid daily up to 800 mg/kg to mice did not reach the LD50 level (50% lethal dose). In human clinical studies, six volunteers received 0.6 g–1.8 g 13-methyltetradecanoic acid daily for one month without any side effects.

The specific branched-chain fatty acids can be, but are not limited to, those obtained by synthesis, or by isolation from said fermentation products. Particularly, the present invention relates to the fermentation products containing these specific branched-chain fatty acids, which have the capability of inhibiting the growth of cancer cells without any toxic or side effects, and the capability of antiaging and immune boosting as well. The present invention also relates to a process of producing fermentation products containing the specific branched-chain fatty acids, using specific bacteria strains, preferably in industrial facilities.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 2A and 2B show the morphological changes of SNU-423 human hepatocellular carcinoma cells undergoing apoptosis under a light microscope; A: untreated; B: treated with 13-methyltetradecanoic acid (60 µg/ml) for 24 hours.

FIGS. 3A and 3B show the morphological changes of SNU-1 human gastric carcinoma cell lines stained with H&E under a light microscope; A: untreated; B: treated with 13-methyltetradecanoic acid (60 µg/ml) for 8 hours.

FIGS. 4A and 4B show the morphological changes of DU-145 human prostate carcinoma cell lines stained with H&E under a light microscope; A: untreated; B: treated with 13-methyltetradecanoic acid (60 µg/ml) for 8 hours.

FIGS. 10A and 10B show detection of apoptotic H1688 cell lines added with POD and substrate under a light microscope; A: untreated; B: treated with 13-methyltetradecanoic acid (60 µg/ml) for 8 hours.

FIGS. 11A and 11B show detection of apoptotic DUI45 cell lines added with POD and substrate under a light microscope; A: untreated; B: treated with 13-methyltetradecanoic acid (60 µg/ml) for 8 hours.

FIGS. 12A and 12B show normal human PBLs added with POD and substrate under light microscope; A: untreated; B: treated with 13-methyltetradecanoic acid (60 µg/ml) for 8 hours.

DETAILED DESCRIPTION OF THE INVENTION

Figure 1A:
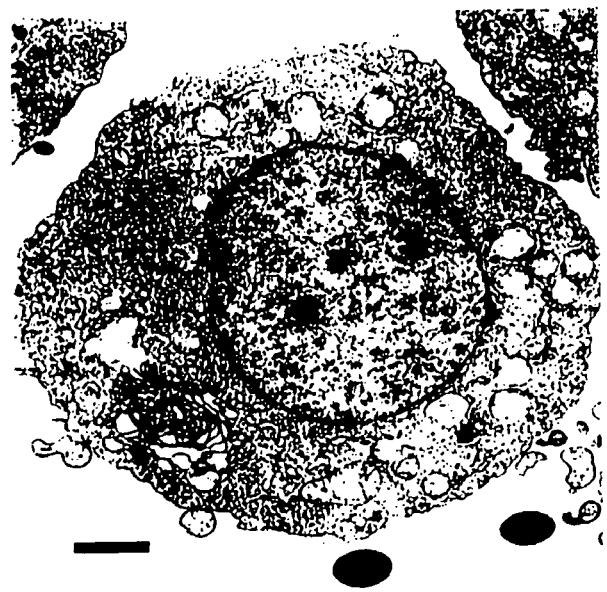
FIGS. 1A and 1B show the morphological changes of K562 human leukemia cells undergoing apoptosis using transmission electron microscope; A: untreated; B: treated with 13-methyltetradecanoic acid (60 µg/ml) for 4 hours.

Definitions of the Specific Branched-Chain Fatty Acids

The present invention relates to specific branched-chain saturated and unsaturated fatty acids, with significant anti-cancer activities, i.e., terminally methyl-branched iso- and anteiso-fatty acids. The present invention also includes any and all derivatives of these fatty acids, so long as the terminally methyl-branched iso- or anteiso-fatty moiety remains. These fatty acids can be characterized by the formula $R_0COOH$, wherein $R_0$ represents a terminally methyl-branched iso- or anteiso-fatty group. By the term "terminally methyl-branched iso" and "terminally methyl-branched anteiso", it is intended that the end of the $R_0$ group farthest away from the COOH group have the following formulae, respectively:

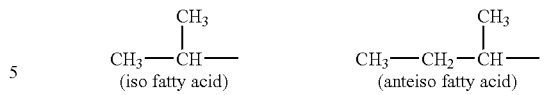

The portion of the fatty group $R_0$ other than the terminally-methyl branched iso- or anteiso-moiety, as described above, is not limited and may be saturated or unsaturated, linear or branched, for example.

An embodiment of the methyl-branched saturated fatty acids wherein the above portion of the fatty group $R_0$ other than the terminally-methyl branched iso- or anteiso-moiety is linear can be described by the formula (I):

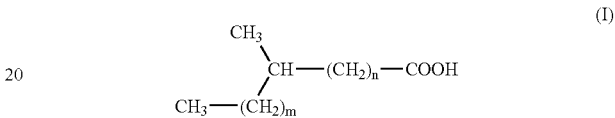

In the above formula (I), m is 0 or 1, and n is an integer. There is no lower or upper limit for n so long as the acid is a fatty acid. Thus, n+m may range as high as 96 or higher, with an upper limit of 46 being preferable. More preferably, n is 7–16.

The methyl-branched unsaturated fatty acids have the above formula, except that n is at least 2, and at least one $CH_2$—$CH_2$ group in $(CH_2)_n$ is replaced with a $CH$=$CH$ group.

The terminally methyl-branched iso-fatty acids are the methyl-branched saturated fatty acids having x carbons and n=x–4, m=0 in the above formula, and known as "iso-Cx" in the present invention. For example, 13-methyltetradecanoic acid is expressed as "iso-C15" and has the formula

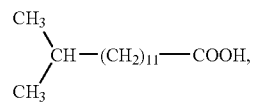

The terminally methyl-branched anteiso-fatty acids are the methyl-branched saturated fatty acids having x carbons and n=x–5, m=1 in the above formula, and known as "anteiso-Cx" in the present invention. For example, 12-methyltetradecanoic acid is expressed as "anteiso-C15" and has the formula

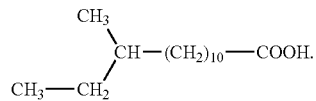

An example of a terminally methyl-branched unsaturated iso-fatty acid of the present invention is

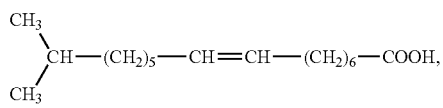

otherwise known as iso-17:1 ω9c.

The present invention also includes pharmaceutically acceptable salts of said terminally methyl-branched iso- and anteiso-fatty acids, which are obtained by reaction with inorganic bases, such as sodium hydroxide, and have the ability to inhibit cancer cell growth. Such compounds include $R_0COONa$ having not less than 12 carbons and $R_0COOK$ having not less than 6 carbons, wherein $R_0$ is as defined above, Na is sodium, and K is potassium.

The present invention also includes pharmaceutically acceptable lipoproteins of said terminally methyl-branched iso- and anteiso-fatty acids, which are obtained by conjugation with proteins, including polypeptides and oligopeptides, and have the ability to inhibit cancer cell growth. Such lipoproteins are well known in the art.

The present invention also includes all pharmaceutically acceptable derivatives other than lipoproteins, such as amides, esters, etc., of said terminally methyl-branched iso- and anteiso-fatty acids, which are obtained by reaction of the fatty acid with the corresponding amine, alcohol, etc. precursor, and have the ability to inhibit cancer cell growth. Such derivatives include, but are not limited to, those that have the formula $R_0CO\text{-}A$, where $R_0$ is as previously defined, and A represents one of the following groups:

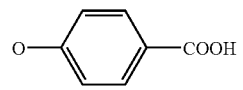
1)

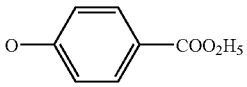
2)

3)

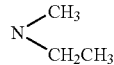
4)

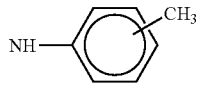
5)

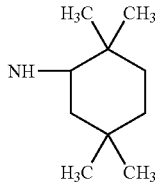
6)

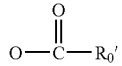
7)

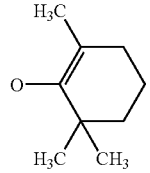
8)

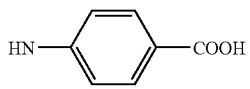
9)

-continued

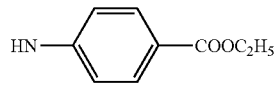
10)

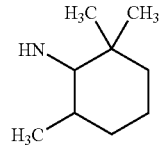
11)

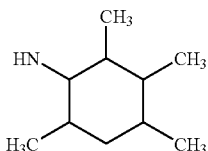
12)

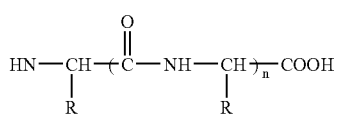
13)

In the above formula 7, $R_0'$ has the same definition as $R_0$ but may be the same or different. In the above formula 13, R is a side chain of an amino acid, and n is 0 or an integer.

The present invention also includes said terminally methyl-branched iso- and anteiso-fatty acids, wherein one or both hydrogens in a —$CH_2$-group is substituted with a group X, such as Cl, I, Br, OH or $NH_2$, and have the ability to inhibit cancer cell growth. Examples of such substituted fatty acids have the formula $R_0CHXCOOH$ or $R_0CX_2COOH$, and more than 8 carbon atoms, wherein $R_0$ is as defined above. Such compounds include:

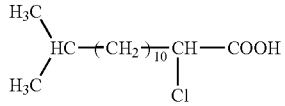

and

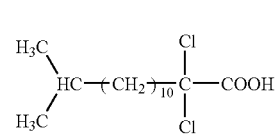

The present invention also includes pharmaceutically acceptable salts, lipoproteins, and other derivatives of the above substituted fatty acids.

The terminally methyl-branched iso- and anteiso-fatty acids of the present invention can be obtained by, but not limited to, isolation from fermentation or incubation products using specific bacteria, or by chemical synthesis, or by extraction from natural materials.

Having generally described this invention, a further understanding can be obtained by reference to certain specific examples which are provided herein for purposes of illustration only and are not intended to be limiting unless otherwise specified.

I. Demonstration of Anticancer Activity and Safety of Specific Branched-Chain Fatty Acids

EXAMPLE 1

Anticancer Activity In Vitro

Samples:

iso-C15, including extracted and synthesized.

The extracted iso-C15 was isolated by HPLC (High Performance Liquid Chromatography) from the fermented solution (fermented using the specific bacteria, *Stenotrophomonas maltophilia* Q-can, and media and production process in present invention).

The synthesized iso-C15 was purchased from Sigma Chemical Company (St. Louis, MO.)

The other specific branched-chain fatty acids tested include:
10-methylundecanoic acid (iso-C12),
11-methyllauric acid (iso-C13),
12-methyltridecanoic acid (iso-C14),
11-methyltridecanoic acid (anteiso-C14),
12-methyltetradecanoic acid (anteiso-C15),
14-methylpentadecanoic acid (iso-C16),
13-methylpentadecanoic acid (anteiso-C16),
15-methylpalmitic acid (iso-C17),
16-methylheptadecanoic acid (iso-C18),
15-methylheptadecanoic acid (anteiso-C18),
17-methylstearic acid (iso-C19),
18-methylnonadecanoic acid (iso-C20).

All the samples above were purchased from Sigma Chemical Company.

Cell Lines:

Human leukemia cell line K562 and human gastric cancer cell line SGC7901.

Methods:

MTT assay was performed to test the cytotoxicity. The K562 and SGC7901 cells were maintained in exponential growth in RPMI 1640 medium supplemented with 15% heat-inactivated newborn calf serum. The cells were plated at a density of $2\times10^4$ cells/100 μl medium/well into 96-well plate with medium containing samples in five final concentrations (7.5, 15, 30, 60 and 90 μg/ml) for iso-C15 (either synthesized or extracted) and one final concentration (30 μg/ml) for the others. The media in control wells contained no samples. The cells were incubated at 37° C. in a highly humidified incubator under 5% $CO_2$ atmosphere for 24 hours. The supernatant was removed by fast inversion of the plate. 20 μl of 5 mg/ml MTT solution were added into each well. Incubation was continued for 4 hours. DMSO 100 μl/well was added and the plate was vibrated for 10 minutes. $A_{570nm}$ was read at the Immunoreader BioTek EL311S.

The inhibition rate (%)=1−(mean $A_{570nm}$ in test wells/ mean $A_{570nm}$ in control wells)

Results:

TABLE 1

Inhibitory rate (%) of synthesized iso-C15* on cell growth

| Cell line | 90 μg/ml | 60 μg/ml | 30 μg/ml | 15 μg/ml | 7.5 μg/ml |
|---|---|---|---|---|---|
| K562 | 85.3 | 83.1 | 71.6 | 50.1 | 26.2 |
| SGC7901 | 68.4 | 63.1 | 50.5 | 27.5 | — |

*the sample was dissolved with 10% ethanol.

TABLE 2

Inhibitory rate (%) of extracted iso-C15* on cell growth

| Cell line | 90 μg/ml | 60 μg/ml | 30 μg/ml | 15 μg/ml | 7.5 μg/ml |
|---|---|---|---|---|---|
| K562 | 87.2 | 83.7 | 72.2 | 51.2 | 27.1 |
| SGC7901 | 68.8 | 62.1 | 51.2 | 28.1 | — |

*the sample was dissolved with 10% ethanol.

TABLE 3

Inhibitory rate (%) of specific branched-chain fatty acids* on K562 cell growth

| Sample | iso-C12 | iso-C13 | iso-C14 | iso-C16 | iso-C17 | iso-C18 |
|---|---|---|---|---|---|---|
| % | 70.69 | 71.03 | 72.15 | 71.58 | 70.79 | 68.39 |

| Sample | iso-C19 | iso-C20 | anteiso-C15 | anteiso-C14 | anteiso-C16 | anteiso-C18 |
|---|---|---|---|---|---|---|
| % | 69.15 | 62.58 | 73.10 | 72.59 | 70.68 | 71.73 |

*the concentration of branched-chain fatty acids was 30 μg/ml; the sample was dissolved with NaOH solution to adjust to pH 7.5.

EXAMPLE 2

Determination of $ID_{50}$, $ID_{75}$ and $ID_{90}$

Samples:

The extracted iso-C15 was isolated by HPLC from the fermented solution (fermented using the specific bacteria, *Stenotrophomonas maltophilia* Q-can, and process of the present invention, infra). The samples were prepared by dissolving them in NaOH solution (adjusted to pH7.5) and 0.5% Tween 80 (Sigma Chemical Company, St. Louis, Mo.).

Cell Lines:

All tumor cell lines were purchased from American Type Culture Collection (ATCC, Manassas, VG) and were cultured as recommended by vendor. Human PBLs were separated from whole blood of healthy individuals by using Ficoll-Hypaque gradients. They were maintained in suspension in RPMI 1640 with 10% plasma from the same individuals. All cell cultures were incubated in a $CO_2$ atmosphere (5%) at 37° C.

Seven human tumor cell lines were studied. K-562 human leukemia and SNU-1 human gastric carcinoma cell lines were cultured in suspension in RPMI 1640 supplemented with 10% heat-inactivated fetal bovine serum (FBS). MCF-7 human breast adenocarcinoma, DU-145 human prostate carcinoma, SNU-423 human hepatocellular carcinoma, HCT 116 human colon carcinoma, and H1688 human small cell lung carcinoma cell lines were propagated as adherent cells in RPMI 1640 supplemented with 10% heat-inactivated FB S (for SNU-423 and H1688), or in McCoy's 5a medium with 10% heat-inactivated FBS (for HCT 116), or in minimum Eagle's medium with 10% heat-inactivated FBS (for MCF-7 and DU-145).

Methods:

All cells in adherent culture were initiated at $5\times10^4$ cells/well in 96-well microplates and treated immediately with iso-C15 at different concentrations (0, 1.5, 3.0, 6.0, 15.0, 30.0, and 60.0 μg/ml) diluted with medium. Both untreated and solvent (NaOH and Tween 80) treated cells served as controls. The treated cells were incubated for 48 hours at 37° C. After incubation, the supernatants were removed and the cells were trypsinized and collected prior to viability assessment by trypan blue dye exclusion.

PBLs, K-562 and SNU-1 cells in suspension culture were seeded in 96-well microplates at a density of $5\times10^4$ cells/well for K-562 and SNU-1, and $1\times10^5$ cells/well for PBLs. iso-C15 were diluted with medium to provide different concentrations (0, 1.5, 3.0, 6.0, 15.0, 30.0, and 60.0 µg/ml). Both untreated and solvent (NaOH and Tween 80) treated cells served as controls. After incubation for 48 hours at 37° C., cells were collected directly from the wells for viability assessment.

The $ID_{50}$, $ID_{75}$ and $ID_{90}$ were determined in duplicate in every set of experiments, and each experiment was repeated three times under identical conditions. $ID_{50}$, $ID_{75}$ and $ID_{90}$ were defined as the concentration of iso-C15 required to kill 50, 75 or 90%, respectively, of cells (compared with that in untreated cells) and computed using CalcuSyn for Windows software (Biosoft, Cambridge UK) based on Median Effect method by Dr. T. C. Chou.

Results:

The cytotoxic activity of iso-C15 was quantified by determining $ID_{50}$, $ID_{75}$ and $ID_{90}$ (µg/ml or µM) in several human hematological and solid tumor cell lines. It is indicated from Table 4 that iso-C15 was active in all tumor cell lines studied. The strongest cytotoxic activities were for MCF-7 human breast adenocarcinoma and K-562 human leukemia. The activities were less for H1688 human small cell lung carcinoma and HCT 116 human colon carcinoma cell lines. In contrast, iso-C15 is not toxic against normal human peripheral blood lymphocytes at concentrations lethal to tumor cells.

canoic acid (anteiso-C15) purchased from Sigma were prepared by dissolving in NaOH solution and then in 0.5% Tween 80 with pH7.5.

Cell Culture:

Human cancer cell lines DU-145 (prostate cancer), K562 (leukemia), HCT116 (colon cancer), H1688 (lung cancer), SUN423 (hepatocarcinoma), MCF7 (breast cancer), CRL-1687 (pancreatic cancer), and SUN-1 (gastric cancer) were obtained from American Type Culture Collection (ATCC). 30 ml blood was collected from a health person and normal peripheral mononuclear cells were separated by Ficoll separation solution (Sigma). All cells were maintained in RPMI 1640, DMEM, or McCoy medium supplemented with 10% FCS, 100 mg/ml streptomycin and 100 u/ml penicillin. Normal human peripheral mononuclear cells, K562 and SUN-1 were suspended cells. After spinning at 1,500 RPM for 5 min, supernatants were discharged and cells were resuspended and expended in fresh medium. The other tumor cell lines were adherent cells and were dispersed with 0.05% trypsin/0.01% EDTA (Irvine Scientific, CA) for expansion. Cells were seeded in T75 flasks at $2\times10^6$ cells/flask in culture medium supplemented with 10% fetal bovine serum and incubated overnight at 37° C. with 5% $CO_2$. The adherent cells attached to the plate were striped with disposable cell scrapers (Fisher Scientific) after treated either with 1% iso-C15, anteiso-C15 or control solution for 1, 2, 4, 8 and 24 hours and then combined with respective float cells. Cells were then prepared for flow cytometry analysis, in situ cell death detection, DNA fragmentation and Western blot assay followed the preparation methods for each assay. Cell

TABLE 4

Cytotoxicity of iso-C15 on human tumor and normal cells in vitro

| cell line | cell type | $ID_{50}$(µg/ml) | $ID_{75}$(µg/ml) | $ID_{90}$(µg/ml) |
| --- | --- | --- | --- | --- |
| MCF-7 | breast carcinoma | 10.03 ± 0.97 | 15.99 ± 1.28 | 25.49 ± 1.68 |
| K-562 | leukemia | 11.45 ± 1.82 | 22.27 ± 4.60 | 43.57 ± 6.71 |
| DU145 | prostate carcinoma | 13.98 ± 2.15 | 40.43 ± 5.72 | 81.87 ± 8.85 |
| H1688 | lung carcinoma | 15.08 ± 1.92 | 35.03 ± 3.59 | 61.37 ± 8.06 |
| HCT-116 | colon carcinoma | 18.49 ± 6.23 | 67.96 ± 8.25 | 108.65 ± 13.35 |
| SNU-1 | gastric carcinoma | 20.77 ± 2.47 | 47.43 ± 4.95 | 80.49 ± 10.03 |
| SNU-423 | hepatocarcinoma | 24.26 ± 3.98 | 70.46 ± 9.36 | 120.77 ± 15.82 |
| PBL | normal human lymphocytes | >400 | | |

EXAMPLE 3

In Vitro Introduction of Apoptosis in Human Tumor Cell Lines and Molecular Pathway Reagents:

RPMI 1640, DMEM and McCoy culture medium, as well as Fetal and calf bovine serums were purchased from Life Technologies (Long Island, N.Y.). Argarose for DNA gel electrophoresis was purchased from FMC, and Acrylamide for Western blot was from Bio-Rad. Antibodies against human c-myc, caspase 3, caspase 8, poly (ADP-ribose) polymerase (PARP), lamins, p53 and retinoblastoma (Rb) were from Oncogene. Chemicals used in buffers and other reagents were from Sigma (St. Louis, Mo.).

13-methyltetradecanoic acid (iso-C15) was chemically synthesized in the inventor's laboratory, as described in Example 5, infra, (purity of 99.8%) and 12-methyltetradepellets treated for 2 and 4 hr with either iso-C15 or control were also stored at −70° C. for future studies of gene regulation.

Methods:

The apoptosis (programmed cell death) of cancer cells induced by specific branched-chain fatty acids was confirmed by: (a) morphology, visualizing morphological changes indicative of apoptosis; (b) flow cytometry, identifying the cells undergoing apoptosis and discriminating apoptosis from necrosis; (c) in situ cell death detection kit, POD, detecting apoptosis induced DNA strand breaks at single cell level; (d) gel electrophoresis assay, visualizing apoptotic DNA fragmentation.

The molecular mechanism of apoptosis induced by specific branched-chain fatty acids was studied using Western blot analysis.

A flow cytometer (FACScan) with Consort 30 software for gating analysis (Becton Dickinson, San Jose, Calif.) was used. The Apoptosis Detection kit (R&D Systems) was used to quantitatively determine the percentage of cells undergoing apoptosis by virtue of their ability to bind annexin V and exclude propidium iodide (PI). Cells were washed in cold PBS twice and resuspended in binding buffer. Fluorescent-labeled annexin V and PI were added to the cells. The cells undergoing apoptosis, expressing phosphotidyiserine on the outer leaflet of cell membranes, would bind annexin V. The cells in later stage of apoptosis or necrosis, with a compromised cell membrane, would allow PI to bind to the cellular DNA. The resulting cells were immediately analyzed by flow cytometer equipped with a single laser emitting excitation light at 488 nm. The annexin V and PI generated signals can be detected in signal detector FL1 and FL2, respectively. Three potential populations of cells can be presented in FL1/FL2 pattern: live cells would not stain with either fluorochrome (zone 3), necrotic and later apoptotic cells would stain with both fluorochromes (zone 2) while cells undergoing apoptosis would stain only with annexin V (zone 4).

In Situ Cell Death Detection Kit, POD (Mannheim Boehringer GmbH) was used to detect the individual apoptotic cells. Cleavage of genomic DNA during apoptosis may yield double-stranded, low molecular weight DNA fragments as well as single strand breaks in high molecular weight DNA. Those DNA strand breaks can be identified by labeling free 3'-OH termini with modified nucleotides in an enzymatic reaction. In this kit terminal deoxynucleotidyl transferase (TdT) is used to label free 3'-OH ends in genomic DNA with fluorescein-dUTP. The incorporated fluorescein is visualized under fluorescence microscope directly. The incorporated fluorescein can also bind to anti-fluorescein antibody POD and be detected by substrate reaction. Stained cells can be analyzed under light microscope.

The gel electrophoresis assay was used for the detection of apoptosis-specific internucleosonal DNA degradation in these cells. Tumor cell pellets, treated with 1% iso-C15 and controls, were lysed in 1 ml hypotonic lysis buffer (10 mM Tris, pH 7.5, 1 mM EDTA, and 0.2% Triton x-100). After centrifuged at 14,000 RPM for 20 min at 4° C., the supernatants were transferred to new tubes and treated with RNase and proteinase K respectively. Supernatants were extracted with phenol/chloroform twice, and fragmented DNA was precipitated in ethanol. Samples were electrophoresed in a 1.5% agarose gel in 1× TAE buffer. The gel was stained with ethidium bromide and destained with distilled water. The fragmented DNA was then visualized under UV light.

For Western blot assay, each cell pellet collected from 1% iso-C15 or control treated cultures was lysed in 150 µl lysis buffer with 0.5% NP-40, 0.5% deoxycholic acid and 1 mM PMSF. The cell lysates were mixed with equal volume 2× Laemmli buffer and boiled for 5 min before loaded into gel wells. Proteins were resolved in an 8% SDS-PAGE gel and transferred to nitrocellulose filter membrane. The filters were blocked with PBS-T (PBS with 0.1% Tween 20) containing 5% nonfat dry milk (Bio-Rad, Richmond, Calif.) for 1 hr and then incubated for 1 hr with proper dilution of one primary antibody in PBS-T containing 2% nonfat dry milk. The filters then were washed in PBS-T 5 min for 6 times and incubated with a 1:8000 dilution of HRP secondary antibody in PBS-T with 2% nonfat dry milk for 1 hr. After 6 washes in PBS-T, immune complexes were visualized on film using the ECL nonradioactive detection system (Amersham, Arlington Heights, Ill.). After detected with one primary antibody, the filter was striped with 0.1 mM Tris pH 7.5 and 0.05 mM β-metacapenanol at 50° C. for 30 min. The filters were washed in 300 ml PBS-T buffer for 10 min twice before blocking with PBS-T with 5% nonfat dry milk. The membranes were then reprobed with monoclonal mouse anti-human β-actin to determine the equal loading of protein for each well.

Results:

Morphological Changes:

The apoptosis of cancer cells is morphologically characterized by cell shrinkage, chromatin condensation, nuclear fragmentation, intact cell membrane and extensive formation of membrane blebs and apoptotic bodies.

Figure 1B:
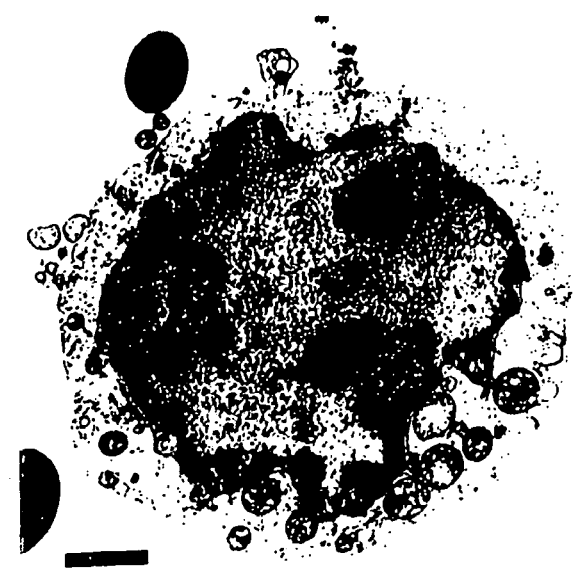

FIG. 1 shows the morphological changes of K562 leukemia cells undergoing apoptosis using transmission electron microscope. Comparing to the untreated intact cell (FIG. 1A), the cell treated with 13-methyltetradecanoic acid (60 µg/ml) for 4 hours (FIG. 1B) exhibits typical apoptotic feature, chromatin condensed into dense masses against the nuclear membrane, membrane intact and cell shrinkage.

FIGS. 2–4 illustrate the morphological changes of cancer cells undergoing apoptosis in a light microscope. Cultured SNU-423 human hepatocellular carcinoma cells treated with anteiso-C15 (60 µg/ml) for 24 hours (FIG. 2B) exhibited cell volume decrease due to shrinkage and bubbles inside the cell, compared to untreated control (FIG. 2A). Cultured SNU-1 human gastric carcinoma cell lines were treated with anteiso-C15 (60 µg/ml) for 8 hours, and cellular morphology was evaluated in preparations stained with H&E (FIG. 3B). Compared to untreated control (FIG. 3A), chromatin condensation and cytoplasmic granularity were noted. Cultured DU-145 human prostate carcinoma cell lines were treated with iso-C15 (60 µg/ml) for 8 hours, and cellular morphology was evaluated in preparations stained with H&E dye (FIG. 4B). Compared to untreated control (FIG. 4A), membrane blebs were noted.

Figure 5A:
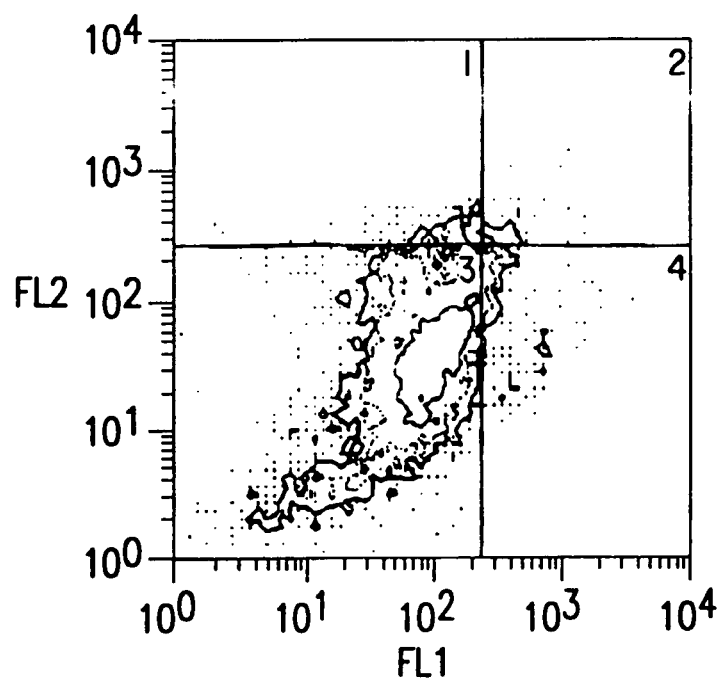
FIGS. 5A and 5B show flow cytometric analysis of K562 human leukemia cells; A: untreated; B: treated with 13-methyltetradecanoic acid (30 µg/ml) for 24 hours.
Figure 5B:
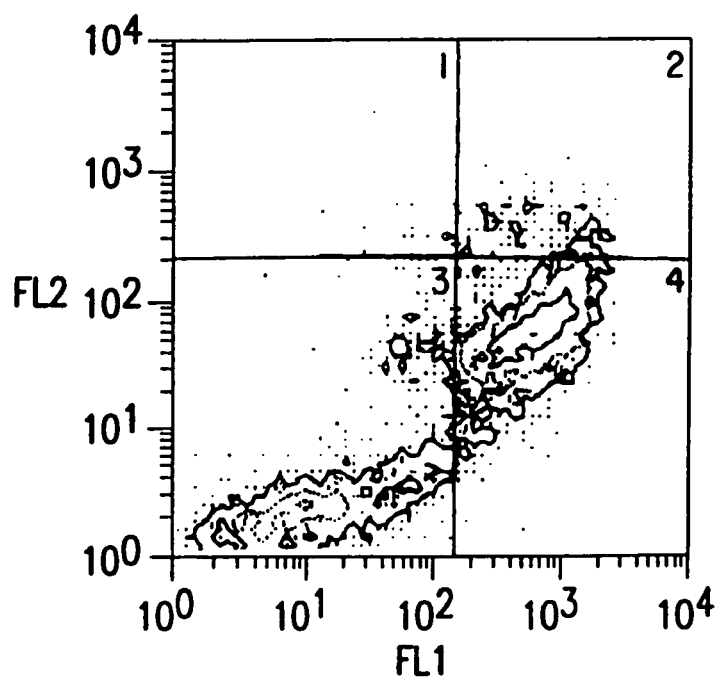
Figure 6A:
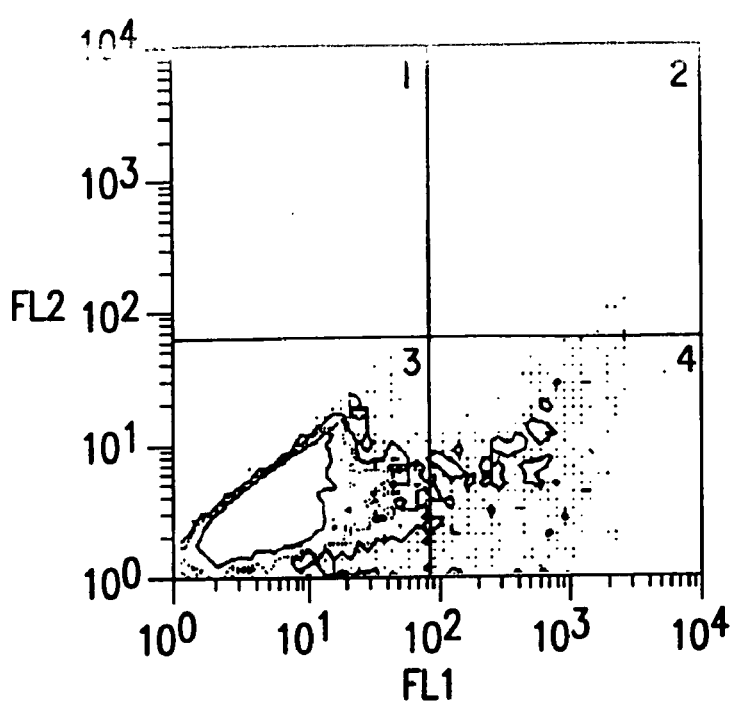
FIGS. 6A, 6B and 6C show flow cytometric analysis of MCF-7 human breast adenocarcinoma cells; A: untreated; B: treated with 12-methyltetradecanoic acid (60 µg/ml) for 4 hours; C: treated with 12-methyltetradecanoic acid (60 µg/ml) for 24 hours.
Figure 6B:
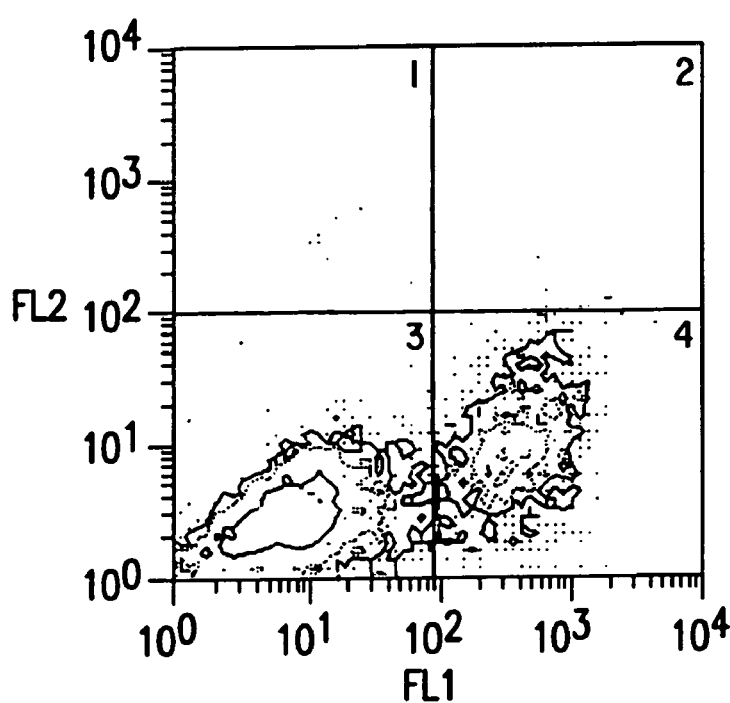
Figure 6C:
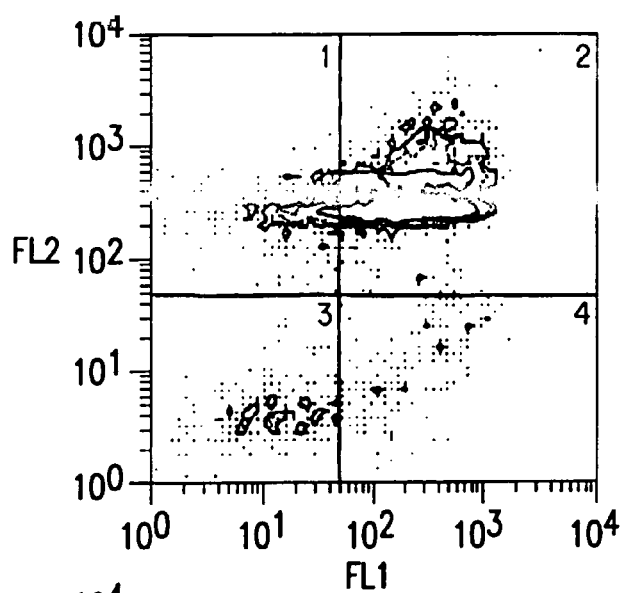
Figure 7A:
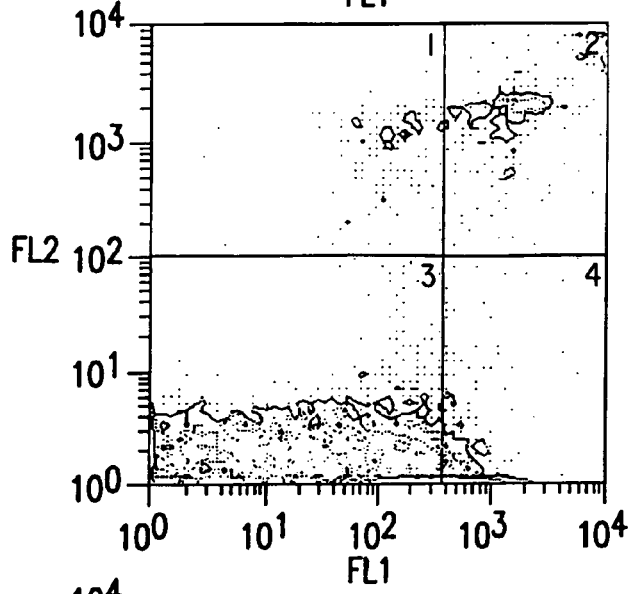
FIGS. 7A and 7B show flow cytometric analysis of normal human peripheral blood lymphocytes (PBLs); A: untreated; B: treated with 13-methyltetradecanoic acid (60 µg/ml) for 24 hours.
Figure 7B:
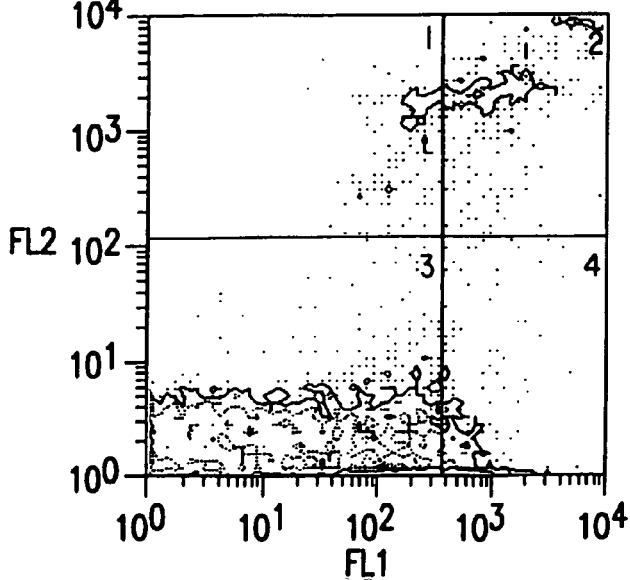

Flow Cytometry:

At least $10^4$ cell events were analyzed. The FL1/FL2 pattern of untreated K562 human leukemia cells (FIG. 5A) revealed the expected distribution of cells in zone 3. After treatment of K562 cells with iso-C15 (30 µg/ml) for 24 hours (FIG. 5B), the majority of the cells were undergoing apoptosis (zone 4, Annexin V positive and PI negative). The kinetic behavior of anteiso-C15 in MCF-7 human breast adenocarcinoma cells was evidenced by FIGS. 6A, 6B and 6C, for treatment of MCF-7 cells with anteiso-C15 (60 µg/ml) for 0, 4 and 24 hours, respectively. After treatment of anteiso-C15 for 4 hours, many cells were undergoing apoptosis (zone 4, FIG. 6B), while after 24 hours the majority of cells had already died (later stage of apoptosis, zone 2, FIG. 6C). The flow cytometric analysis of untreated normal human PBLs (FIG. 7A) and treated PBLs with iso-C15 (60 µg/ml) for 24 hours (FIG. 7B) resulted in nearly identical FL1/FL2 patterns (zone 3, viable and not undergoing apoptosis), revealing no significant effects by iso-C15 on normal human lymphocytes.

In Situ Cell Death Detection:

Four human tumor cell lines, K-562 human leukemia, SNU-1 human gastric carcinoma cell lines, MCF-7 human breast adenocarcinoma and H1688 human small cell lung carcinoma cell lines, as well as Human PBLs were treated with iso-C15 (60 µg/ml).

Figure 8A:
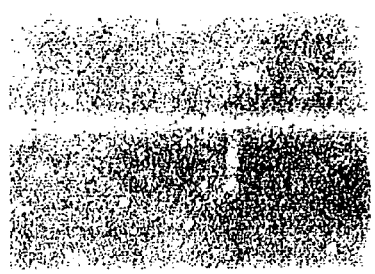
FIGS. 8A and 8B show detection of apoptotic SNU-1 cell lines added with TUNEL-(TdT-mediated dUTP nick end labeling) reaction mixture under a fluorescence microscope; A: untreated; B: treated with 13-methyltetradecanoic acid (60 µg/ml) for 8 hours.
Figure 8B:
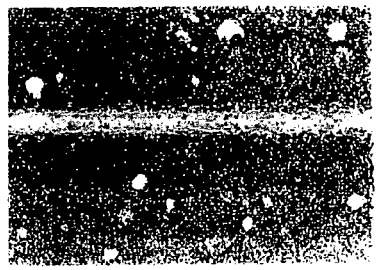

SNU-1 cells treated with iso-C15 for 8 hours were added with TUNEL-reaction mixture and incubated 60 min at 37° C. After washing with PBS for three times, cell morphology was analyzed directly under fluorescence microscopy. Several yellow fluorescent spots of apoptotic cells were noted in cells treated for 8 hours (FIG. 8B), comparing to untreated ones (FIG. 8A).

Figure 9A:
FIGS. 9A, 9B and 9C, show detection of apoptotic K-562 cell lines added with peroxidase (POD) and substrate under a light microscope; A: untreated; B: treated with 13-methyltetradecanoic acid (60 µg/ml) for 2 hours; C: treated with 13-methyltetradecanoic acid (60 µg/ml) for 4 hours.
Figure 9B:
Figure 9C:
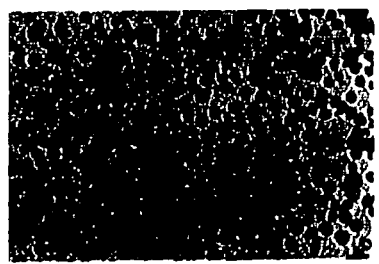

H1688, K-562 and DU145 human cancer cells and normal human PBLs were added with POD and incubated 30 min at 37° C., washed three times with PBS, then reacted with substrate AEC and incubated for 10 min at room temperature. The cells were analyzed under light microscope. Comparing K-562 leukemia cells untreated (FIG. 9A) and treated for 2 and 4 hours (FIGS. 9B and 9C), it is found that some cells started apoptosis (stained red) 2 hours after treatment and the number of apoptotic cells increased with exposure time. The apoptotic H1688 cancer cells (stained red) were found after 8 hours of treatment (FIG. 10B) comparing to untreated (FIG. 10A). Some stained apoptotic DU145 cancer cells were shown 8 hours after treatment (FIG. 11B) and no stained cells in untreated control (FIG. 11A). In contrast, untreated and 8-hour treated PBLs were almost the same (FIGS. 12A and 12B), and few stained apoptotic cells were seen. It is evidenced that iso-C15 induces apoptosis of cancer cells but not normal human cells.

Figure 13:
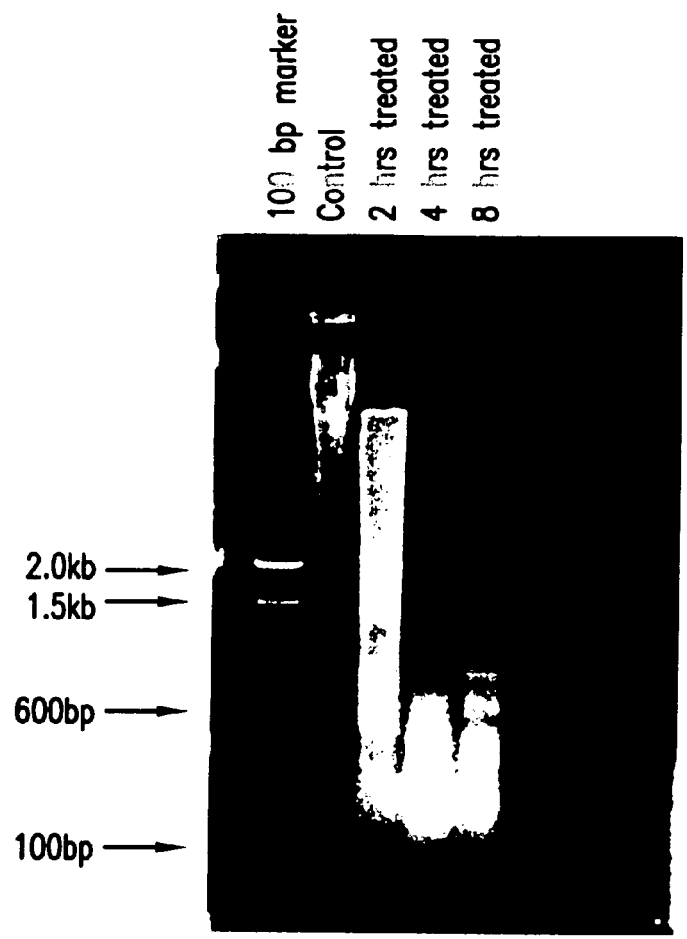
FIG. 13 shows DNA fragmentation gel electrophoresis of K562 human leukemia cells undergoing apoptosis, which were treated with 13-methyltetradecanoic acid (60 µg/ml).

DNA Fragmentation Gel Electrophoresis:

DNA fragmentation electrophoresis is one of most common applied methods to illustrate the apoptotic changes in experimental cells. Results for K562 leukemia cell line treated with iso-C15 (60 μg/ml) were shown in FIG. 13. The lane of control treated for 8 hours showed only DNA smear. The fragmented low molecular weight DNA bands were seen at 2 hour and were prominent at 8 hour treated. The appearance of an oligonucleosomal ladder in treated cells indicated the break of double-stranded DNA due to apoptosis induced by iso-C15.

Western Blot Analysis:

The Western blot analysis results (FIGS. 14–17) are used as examples to reveal the signal transduction pathway for specific branched-chain fatty acid to activate apoptosis of cancer cells.

Figure 14:
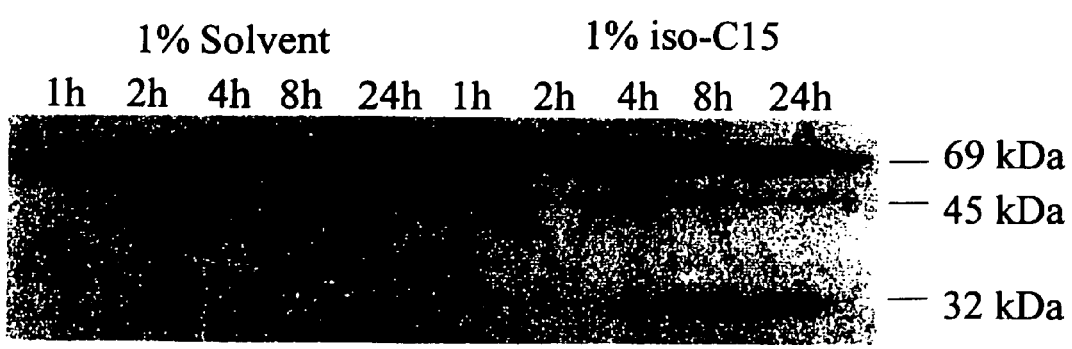
FIG. 14 shows caspase target protein Lamin B cleavage in apoptotic SNU-423 human hepatocellular carcinoma cells treated with 13-methyltetradecanoic acid (60 µg/ml).
Figure 15:
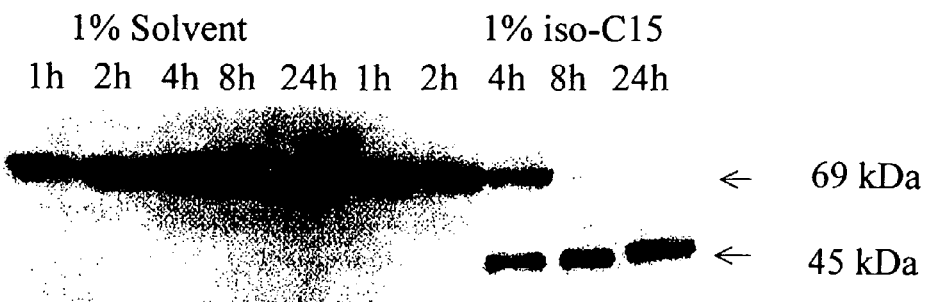
FIG. 15 shows caspase target protein Lamin B cleavage in apoptotic K562 human leukemia cells treated with 13-methyltetradecanoic acid (60 µg/ml).
Figure 16:
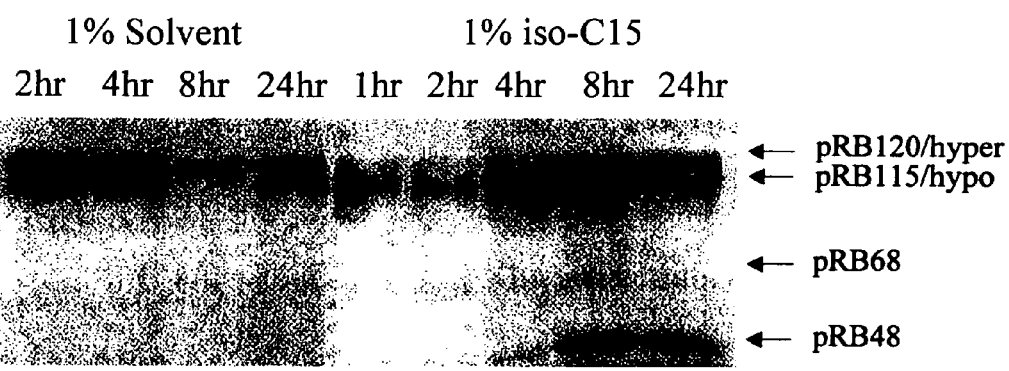
FIG. 16 shows caspase target protein Rb hypophoshorylation and cleavage in apoptotic SNU-423 human hepatocellular carcinoma cells treated with 13-methyltetradecanoic acid (60 µg/ml).
Figure 17:
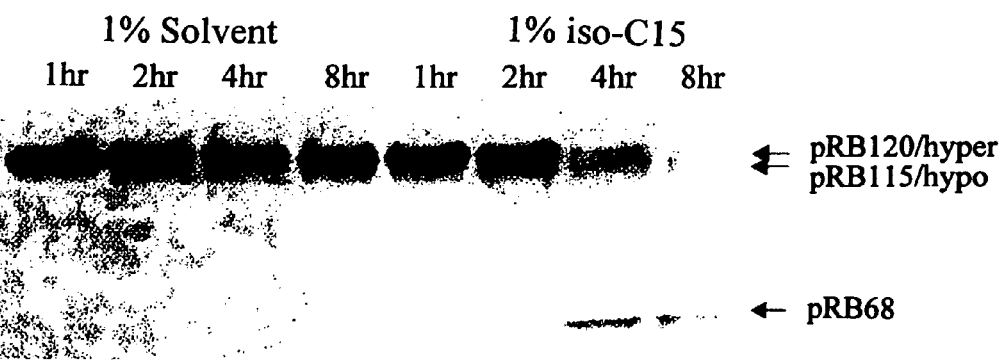
FIG. 17 shows caspase target protein Rb hypophoshorylation and cleavage in apoptotic K562 human leukemia cells treated with 13-methyltetradecanoic acid (60 µg/ml).

The cleavages of Lamin B, a caspase target protein, in apoptotic SNU-423 human hepatocellular carcinoma cells and K562 human leukemia cells were shown in FIGS. 14 and 15, respectively. The cells were treated with 1% control solution and 1% iso-C15 for the length of time indicated. Cell lysates were separated by SDS-PAGE. Lamin B was detected by immunoblotting with a monoclonal antibody. The cleaved 45 kDa and 32 kDa products were shown in FIG. 14, and the cleaved 45 kDa products in FIG. 15. The cleavage of caspase target protein Lamin B suggested the activation of the caspase cascade during apoptosis. The Western blot analysis of RB protein in SNU-423 and K562 cells were shown in FIGS. 16 and 17, respectively. The results showed that iso-C15 induced the change of hyperphosphorylated RB (pRB120/hyper) to hypophosphorylated form (pRB115/hypo), and also induced the cleavage of full length RB to pRB68 kDa fragment in FIGS. 16 and 17, and even smaller pRB48 kDa fragment in FIG. 16.

EXAMPLE 4

Anticancer Activity In Vivo

A. Determination of $LD_{50}$

Materials and Methods:

13-methyltetradecanoic acid (iso-C15) purchased from Sigma (St. Louis, Mo.) was prepared by dissolving in NaOH solution and then in 0.35% Tween 80 with pH7.5.

ICR mice weighing 20.5–22.5 g of both sexes were treated with iso-C15 i.p. qd×3 in test groups and with solvent of same dose as in a control group. The doses ranged from 10 to 800 mg/kg of iso-C15 and two mice were included in each dose group (10 mg/kg, 20 mg/kg, 40 mg/kg, 80 mg/kg, 160 mg/kg, and 800 mg/kg). The general condition of these mice were monitored daily for seven days.

Results:

No mice died after seven-day administration of iso-C15 of dose up to 800 mg/kg. It is shown that iso-C15 is basically not toxic to mice and 50% lethal dose ($LD_{50}$) was not determined.

B. Efficacy Evaluation of Iso-C15 in Orthotopic Nude Mice Model of Human Prostate Carcinoma DU145

Material and Methods:

13-methyltetradecanoic acid (iso-C15) was chemically synthesized in the inventor's laboratory, as described in Example 5, infra, (purity of 99.8%) was prepared by dissolving in NaOH solution and then in 0.35% Tween 80 with pH7.5.

Total of 24 male athymic BALB/c nude mice between 4 and 5 weeks of age were bred and maintained in specific pathogen free condition.

Human prostate carcinoma DU145 tumor was implanted and maintained subcutaneously in the flank of athymic nude mice. Prior to orthotopic implantation, the tumor was harvested in log phase. The peripheral tumor tissue was collected and minced to small pieces of one cubic millimeter each.

The mice were anesthetized for surgical orthotopic implantation. A small incision was made along the midline of the lower abdomen. After proper exposure of the bladder and prostate, the capsule of the prostate was opened and three pieces of DU145 tumor fragments were inserted into the capsule. The capsule was then closed using 8-0 suture, and the abdomen was closed using a 6-0 surgical suture.

The mice bearing orthotopic DU145 were randomly divided into control and test groups of eight mice each at the second day after tumor implantation. The iso-C15 prepared above at doses 35 and 70 mg/kg and PBS were administered by gavage once a day in low dose and high dose test groups and control group, respectively, for 43 days.

All the mice were sacrificed by $CO_2$ inhalation at day-40 after the start of treatment. The weights of primary tumors and bodies were measured. Tissue samples of the primary tumors were processed through standard procedures of hematoxylin and eosin staining for microscopic examination.

The tumor inhibition rates (TIR) were determined by comparing the mean tumor weight of the test groups (T) with that of the control group (C) and expressed as a (C)–T)/C percentage, and were analyzed by Student's test for statistical significance.

Results:

Very promising antitumor efficacy was observed for iso-C15 at doses 35 mg/kg and 70 mg/kg in this nude mouse model of human prostate carcinoma DU145 with the tumor inhibition rates 54.8% ($p<0.05$) and 84.6% ($p<0.01$) as shown in Table 5.

TABLE 5

Efficacy of iso-C15 on primary tumor and body weight in nude mouse model of human prostate carcinoma DU145

| Group | Route | No. of mice | Mean tumor weight (mg) | TIR (%) | P |
|---|---|---|---|---|---|
| Control | Oral | 8 | 1,090.75 | — | — |
| Low dose, 35 mg/kg | Oral | 8 | 493.25 | 54.8 | 0.042 |
| High dose, 70 mg/kg | Oral | 8 | 168.00 | 84.6 | 0.007 |

Figure 18:
FIG. 18 shows comparison of the tumors removed from the mice of two treated groups and control group of human prostate cancer DU145 nude mice model.

For comparison, all the primary tumors after removal from the nude mice are shown in FIG. 18, where it is noted that the implanted tumor did not grow in four mice in the high dose treatment group. There are no signs of toxicity, as judged by the body weight curve and histology slides.

C. Efficacy Evaluation of Iso-C15 in Orthotopic Nude Mice Model of Human Hepatocellular Carcinoma LCI-D35

Material and Methods:

13-methyltetradecanoic acid (iso-C15) was chemically synthesized in the inventor's laboratory, as described in Example 5, infra, (purity of 99.8%), was prepared by dissolving in NaOH solution and then in 0.35% Tween 80 with pH7.5.

Total of 16 male and female athymic BALB/c nude mice between 4 and 5 weeks of age were bred and maintained in specific pathogen free condition.

Human hepatocellular carcinoma LCI-D35 was originally obtained from the primary tumor of a 45-year-old female patient. The tumor was implanted and maintained subcutaneously in athymic nude mice. Prior to orthotopic implantation, the tumor was harvested in log phase. The peripheral tumor tissue was collected and minced to small pieces of one cubic millimeter each.

The mice were anesthetized for surgical orthotopic implantation. A small incision was made along the midline of the upper abdomen. The left lobe of the liver was exposed and a small incision was made on the liver surface. Two of the tumor fragments above were sutured into the incision using 8-0 suture. The abdomen was then closed using a 6-0 surgical suture.

The mice bearing orthotopic LCI-D35 were randomly divided into control and test groups of eight mice each at the second day after tumor implantation. The iso-C15 prepared above at dose 70 mg/kg and PBS were administered by gavage once a day in the test and control group, respectively, for 40 days.

All the mice were sacrificed by $CO_2$ inhalation at day-40 after the start of treatment. The weights of primary tumors and bodies were measured. Tissue samples of the primary tumors were processed through standard procedures of hematoxylin and eosin staining for microscopic examination.

The tumor inhibition rates (TIR) were determined by comparing the mean tumor weight of the test groups (T) with that of the control group (C) and expressed as a (C)–T)/C percentage, and were analyzed by Student's test for statistical significance.

Results:

Very promising antitumor efficacy was observed for iso-C15 at dose 70 mg/kg in this nude mouse model of human hepatocellular carcinoma LCI-D35 with a tumor inhibition rate 64.9% (p<0.01), as shown in Table 6.

TABLE 6

Efficacy of iso-C15 on primary tumor and body weight in nude mouse model of human hepatocellular carcinoma LCI-D35

| group | dose | route | mice No. in./fi. | body weight in./fi. | tumor weight mean ± SD (g) | TIR (%) | p |
|---|---|---|---|---|---|---|---|
| PBS | — | oral | 8/8 | 17.31/21.50 | 0.202 ± 0.117 | — | |
| iso-C15 | 70 mg/kg | oral | 8/8 | 18.23/21.75 | 0.071 ± 0.052 | 64.9 | 0.0086 |

Figure 19:
FIG. 19 shows comparison of the tumors removed from the mice of treated group and control group of human hepatocellular carcinoma LCI-D35 orthotopic nude mice model.

For comparison, all the primary tumors after removal from the nude mice are shown in FIG. 19, where it is noted that the implanted tumor did not grow in two mice in the treatment group. There are no signs of toxicity, as judged by the body weight curve and histology slides.

D. Human Clinical Studies on the Safety of Iso-C15

Material and Method:

Chemically synthesized iso-C15 of 99.8% purity were prepared in 0.20 g capsules. Six healthy adult volunteers (4 male, 2 female) of average age 35.6 were divided into three groups, and orally received iso-C15 capsules for thirty days. Low dose group: one case, 0.6 g daily; middle dose group: two cases, 1.2 g daily; high dose group: three cases, 1.8 g daily.

The examinations were carried out before, during and after experiment, including physical examinations, blood and urine routine examinations, function of heart, liver and kidney, X-ray radioscopy of lung and subjective symptom.

Results:

The effects of iso-C15 on blood routine and platelet shown in Table 7 indicated significant increase of white blood cells (WBC) and granulocyte (GRAN), while no significant changes of red blood cells (RBC), hemoglobin (HB) and platelet (PLT). No abnormality was observed from alanine aminotransferase (ALT) and blood urea nitrogen (BUN) for all subjects, as shown in Table 8. No abnormality was observed on heart and lung from electrocardiogram (EKG) and X-ray radioscopy, and no abnormality on urine routine as well.

TABLE 7

Effects of iso-C15 on blood routine and platelet

| | | | $X \pm SD$ | | |
|---|---|---|---|---|---|
| Item | Case | Before test | | After test | p |
| WBC | 6 | $5.80 \pm 0.95 \times 10^9/L$ | | $7.50 \pm 0.71$ | 0.0072 |
| GRAN | 6 | $3.20 \pm 0.59 \times 10^9$ | | $3.80 \pm 0.89$ | 0.0311 |
| RBC | 6 | $4.64 \pm 0.40 \times 10^{12}/L$ | | $4.62 \pm 0.69$ | 0.8719 |
| HB | 6 | $122.00 \pm 10.40/L$ | | $128.00 \pm 16.90$ | 0.1839 |
| PLT | 6 | $203.0 \pm 33.3 \times 10^9/L$ | | $232.0 \pm 52.1$ | 0.0809 |

TABLE 8

Effects of Iso-C15 on Liver And Kidney Functions

| | | | $X \pm SD$ | | |
|---|---|---|---|---|---|
| Item | Case | Before Test | | After Test | p |
| ALT | 6 | $15.17 \pm 8.70 \ \mu/L$ | | $15.00 \pm 10.33$ | 0.4398 |
| BUN | 6 | $6.69 \pm 2.14$ mmol/L | | $6.47 \pm 1.72$ | 0.02850 |

It indicated a wide safety range of 13-methyltetradecanoic acid for oral administration (0.6 g–1.8 g daily for one month) without any toxicity effects. It also showed an increase of white blood cells and granulocytes, indicating an immune boosting effect.

The branched-chain fatty acids can be administered in the form of liquid, powder, tablet, capsule, injection or encapsulated with liposome, to be delivered by bypassing the digestive tract, or directly into the bloodstream. They also can be used as a topical drug for skin cancer or other skin diseases.

E. Chemoprevention of 7,12-Dimethylbenz(a)-Anthracene (DMBA)-Induced Mammary Carcinogenesis in Rats by Iso-C15

Materials and Method:

13-methyltetradecanoic acid (iso-C15) was prepared by dissolving in NaOH solution and then in 0.35% Tween 80 with pH 7.5.

Fifty female Sprague-Dawley rats were maintained on laboratory chow. At 50 days of age, rats were given a single dose (5 mg) of DMBA (Sigma Chemical Co., St. Louis. Mo.) via an intragastric tube. Seven days after DMBA administration, the rats were randomly divided into two groups of 25. Each rat in the control group was given 0.5 ml of 0.35% Tween 80 five times a week via an intragastric tube throughout the experiment, while each in the test group was given 0.5 ml iso-C15 solution of concentration 0.7%, five times a week. Food and water were available ad libitum. Twenty weeks after DMBA administration, all rats were scarified, and all palpable tumors were removed.

Results:

Results:

The results assessed the protective effect of iso-C15 during the tumor promotion stage. At the termination of the experiment, the animals in the iso-C15-treated group showed a 40% reduction in tumor incidence. The iso-C15-treated group also showed 90% reduction of tumor volume comparing to the vehicle-treated. i.e. control, group.

II. Production Process of Specific Branched-Chain Fatty Acids

The present invention includes methods of making said specific branched-chain fatty acids with anticancer activities.

The specific branched-chain fatty acids of the present invention can be isolated from natural resources occurring including, but not limited to, the organisms containing the specific branched-chain fatty acids, such as animal fats or phytol of green plants.

The specific branched-chain fatty acids of the present invention can also be synthesized by chemical or biological methods. The classical Kolbe's synthesis methods of branched-chain fatty acids are well known and a specific example of a method for electrosynthesis of 13-methyltetradecanoic acid is provided in the example below. The biosynthesis methods for making the specific branched-chain fatty acids of the present invention are fermentation or incubation processes using specific bacteria strains contain-

TABLE 9

Effects of iso-C15 on tumorigenesis of DMBA-induced mammary cancer in rats

| Group | Case | No. of rats with tumors | tumor incidence | No. of tumors | No. of tumors per rat | No. of tumors/ tumor bearing rat | mean tumor weight (g) |
|---|---|---|---|---|---|---|---|
| control | 25 | 21 | 84% | 52 | 2.1 ± 1.7 | 2.5 ± 2.4 | 2.4 ± 5.8 |
| iso-C15 | 25 | 3 | 12% | 4 | 0.2 ± 0.1 | 1.3 ± 0.5 | 0.8 ± 1.3 |

It is shown in Table 9 that iso-C15 significantly reduced the incidence of mammary cancer. Iso-C15 has offered prevention in experimental mammary carcinogenesis. It caused slower tumor growth, though it could not achieve a complete prevention.

F. Chemoprevention of Ultraviolet B Ray (VB)-Induced Skin Cancer by Iso-C15

Materials and Method:

13-methyltetradecanoic acid (iso-C15) was prepared by dissolving in NaOH solution and then in 0.8% Tween 80 with pH 7.5, with resulting concentration 10%.

Forty female SKH-1 hairless mice were divided into control and test groups, with 20 in each. The mice in both groups were treated topically once with 5.12 µg of DMBA dissolved in 200 µl acetone per mouse to achieve tumor initiation. One week later (day 8), animals in the test group were applied topically with 200 µl iso-C15 per application per mouse per day. The control group received 200 µl Tween 80 per application per mouse per day. Thirty minutes later, the animals in both groups were exposed to UVB (290–320 nm) radiation at a dose of 180 mJ/cm$^2$ per day to achieve UVB radiation-induced tumor promotion. The iso-C15 or vehicle treatments followed by UVB irradiation were performed twice a week up to 30 weeks from the start of UVB exposure. The animals were evaluated for tumor incidence at the end of 30 weeks.

ing a high percentage of specific branched-chain fatty acids in their cellular lipids. A process for making a fermentation solution containing specific branched-chain fatty acids and having anticancer functions is also provided in the examples below.

EXAMPLE 5

Electrolytical Synthesis of 13-Methyltetradecanoic Acid 13-methyltetradecanoic acid is synthesized electrolytically from isovaleric acid and methyl hydrogen dodecanedioate in methanolic solution, based on Kolbe electrolysis.

Dimethyl dodecanedioate was prepared from dodecanedioic acid by esterification with 5 parts v/w methanol containing 5% w/v concentrated sulfuric acid. The dimethyl ester, after purification by vacuum fractional distillation, was converted to the mono-ester using the theoretical quantity of kalium hydroxide in anhydrous methanol. The methyl hydrogen dodecan-1,12-dioate was purified by distillation.

The electrolytic coupling reaction was carried out with mono-ester and a 2-fold molar excess of isovaleric acid dissolved in methanol containing sodium methoxide, using 2×10 cm$^2$ platinum electrodes. The reaction mixture was stirred and maintained at 50° C. by water cooling until the solution became alkaline. Electrode polarity was reversed every 30 min to prevent the built-up of deposits on the electrode surfaces.

After electrolysis the reaction mixture was cooled to room temperature and the by-products, dimethyl docosanedioate, which precipitated was removed by filtration. The filtrate was acidified with acetic acid and the methanol removed by rotary evaporation under reduced pressure. The crude methyl 13-methyltetradecanoate was purified by fractional distillation. Finally the methyl ester was hydrolyzed by refluxing with excess 10% w/v sodium hydroxide in ethanol/water (50:50, v/v). After cooling and acidification, the free acid was extracted with diethyl ether and purified by vacuum distillation.

EXAMPLE 6

Process for Making a Fermentation Solution Containing Specific Branched-Chain Fatty Acids A process for making a fermentation solution containing a high percentage of specific branched-chain fatty acids is exemplified below.

The starter cultures grow in a slant agar medium for 24 hours first, then are inoculated onto the liquid medium in the culture flask and cultured on the incubator shaker for 24 hours. Next, the liquid cultures in the flask are inoculated onto a seeding tank at an inoculating rate of 0.1–0.5% (w/w). The cultures, after fermenting in the seeding tank for 24 hours, are replaced onto production fermenters to ferment for 48 hours, with aseptic airflow passing the mass. Generally, the magnification ration from seeding tank to production fermenter is about ten. The incubation conditions are aeration rate of 1: 0.6–1.2 (mass/air) v/v in, agitation speed of 180–260 rpm, and the temperature of 28–38° C.

After the incubation is finished, the resulting culture solution is autoclaved at 100° C. for 30 minutes, and then the harvested solution can be packaged and autoclaved at 120° C. The resulting product is an oral nutritional liquid with anticancer and salutary functions for human use.

Alternative products can be obtained by a different procedure including, but not limited to, the method below. After the incubation is finished, an appropriate amount of hydrochloric acid can be added to the resulting culture solution to lower the pH to 3–4, and it is autoclaved at 100° C. for 30 minutes and the cooled solution is finally centrifuged. The resulting supernatant, in which soy saponin is the predominant component, can be used to manufacture a nutrient drink with various tastes. Then the same volume of 95% aqueous ethyl alcohol and the same volume of 2 N NaOH can be added to the resulting precipitate, which is then agitated and then heated at 100° C. After cooling and centrifuging, while collecting the resulting supernatant for later use; the same volume of 1 N HCl can be added to the remainder precipitate and heated for 5 minutes at 80° C. After cooling and centrifuging, the resulting supernatant is collected. The two fractions of supernatants are combined together and the pH adjusted to 9.0, to thereby obtain a concentrated oral nutritional liquid product containing various branched-chain fatty acids, and soy isoflavones such as saponin, daidzein, genistein, and other anticancer substances.

Another procedure is, after the incubation is completed, directly atomize and dry the solution into a powder product, and encapsulate the powder into capsules or make tablets.

The specific branched-chain fatty acids can be isolated from the fermented solution using well-known methods in the art for isolating cellular fatty acid. The isolated active branched-chain fatty acids are reprocessed in various formulations. The formulations of the present invention comprise at least one specific branched-chain fatty acid or its pharmaceutically acceptable salt including sodium salt. They can be contained in an ampule for injection or transfusion, especially for advance stage cancer patients. They may also be mixed with a carrier, or diluted by a carrier, or enclosed or encapsulated by a digestible carrier in the form of a capsule, sachet, cachet, paper or other container or by a disposable container such as an ampule. The carrier or diluent may be a solid, semi-solid or liquid material, which serves as a vehicle, excipient or medium for the active therapeutic substance.

In the process described above, soybean media are used. The components are listed by weight with water making up the reminder. Proper amounts of trace elements necessary for the human body in addition to said nutritional components are added.

| Soybean medium | |
|---|---|
| Soybean | 5–10% |
| or soybean milk or bean cake (by soybean wt.) | 5–15% |
| Yeast extract | 0.02–0.5% |
| or yeast powder | 0.02–0.5% |
| $CaCO_3$ | 0.05–0.25% |
| $K_2HPO_4$ | 0.02–0.10% |
| $MgSO_4$ | 0.01–0.05% |
| NaCl | 0.01–0.04% |
| $Na_2MoO_4$ | 5.0–30 ppm |
| $ZnSO_4$ | 2.5–15 ppm |
| $CoCl_2$ | 5.0–20 ppm |

In addition to the bacteria which have been identified as containing a high percentage of branched-chain fatty acids, such as the genus *Stenotrophomonas, Xanthomonas, Flavobacterium, Capnocytophaga, Altermonas, Cytophage, Bacillus, Chryseobacterium, Empdobacter, Aurebacterium, Sphinggobacterium, Staphylococcus, Azotobacter* and *Pseudomonas*, the bacteria of the present invention also include all other bacteria strains containing branched-chain fatty acids.

The products in the form of oral liquids, capsules, tablets or injections, produced using said bacteria and media, with the process of making of the present invention, have anticancer functions and other nutritional effects for human and animals.

III. Anticancer Function of Fermentation Solutions Containing Specific Branched-Chain Fatty Acids The said fermentation solutions are produced using specific bacteria strains, which contain a high percentage of branched-chain fatty acids, and nutritive media, such as soybean media, and processes of the present invention. The fermentation solution contains various specific branched-chain fatty acids with significant anticancer activity, and other nutritional composites from soybean or other media and bacteria metabolite. To demonstrate their anticancer function, the following animal experiments and clinical trials are presented. As an example of said fermentation solutions, in the following experiments, the fermentation solution, named Q-can oral liquid, was used.

Q-can oral liquid was produced using *Stenotrophomonas maltophilia* strain Q-can as the production strain, while using the soybean medium above and the process of making of the present invention. Parallel animal experiments and clinical trials were also conducted using its atomized capsule product. The same conclusions were obtained as for Q-can oral liquid product.

The production strain, *Stenotrophomonas maltophilia* Q-can, has all the identifying characteristics of the sample on deposit with American Type Culture Collection, 10801 University Boulevard, Manassas, Va. 20110-2209, and assigned ATCC 202105. The bacterial characteristics was identified by ATCC as following:

The cellular morphology is motile, non-sporing, Gram negative, and aerobic rods.

The colony morphology is the following: Colonies at 24 hours on ATCC medium #3 (nutrient agar) were I, −90% circular (approximately 1 mm in diameter) with entire margins and convex elevation, rough surface, semi-translucent, light beige color: II, −10% small circular (<1 mm in diameter), entire margins, convex elevation, semi-translucent, smooth surface and darker than I. Same characteristics were found when grown on ATCC medium #18 (T-soy agar). #44 (BHI agar) and #260 (Sheep blood agar). Both colonies were characterized and found to be the same.

The cellular fatty acid composition of *Stenotrophomonas maltophilia* Q-can is the following:

| Fatty Acid (% of total) | | | |
|---|---|---|---|
| straight-chain acid* | | branched-chain acid** | |
| 10:0 | 0.48 | i11:0 | 3.21 |
| 14:0 | 3.14 | i13:0 | 0.50 |
| 15:0 | 0.33 | i15:0 | 39.34 |
| 16:0 | 5.52 | a15:0 | 7.44 |
| 16:1 ω9c | 3.37 | i15:1 | 1.02 |
| 16:1 ω7c | 12.58 | i16:0 | 0.88 |
| hydroxy acid | | i17:0 | 3.68 |
| 3OH-10:0 | 0.12 | i17:1 ω9c | 5.27 |
| 3OH-i11:0 | 1.51 | i19:0 | 0.33 |
| 3OH-i12:0 | 2.68 | | |
| 3OH-i13:0 | 3.57 | | |
| 2OH-13:0 | 0.29 | | |

*The number to the left of the colon refers to the number of carbon atoms, the number to right refers to the number of double bonds.
**i = iso fatty acids, a = anteiso fatty acids.

Since the fatty acid composition of bacteria is influenced by biosynthesis conditions including temperature and pH, the data above may be considered as a typical value.

The typical fatty acid contents in 500 ml of Q-can oral liquid are the following:

| straight-chain acid | | branched-chain acid | |
|---|---|---|---|
| 10:0 | 2.0–2.7 mg | i11:0 | 11.2–15.4 mg |
| 12:0 | 2.9–4.0 mg | i15:0 | 106.0–145.8 mg |
| 14:0 | 13.0–17.7 mg | i16:0 | 3.1–4.3 mg |
| 15:0 | 2.8–3.8 mg | i17:0 | 12.4–17.0 mg |
| 16:0 | 251.7–346.1 mg | i19:0 | 2.2–3.0 mg |
| 17:0 | 2.9–4.0 mg | a15:0 | 23.4–32.1 mg |
| 18:0 | 75.6–104.0 mg | i17:1 ω9c | 4.1–5.7mg |
| 20:0 | 5.5–7.6 mg | | |
| 12:1 ω8c | 4.3–5.9 mg | hydroxy acid | |
| 16:1 ω7c | 21.0–28.9 mg | 3OH-i11:0 | 6.3–8.6 mg |
| 18:1 ω9c | 488.8–672.0 mg | 3OH-12:0 | 12.0–16.5 mg |
| 18:2 ω6c | 825.9–1135.6 mg | 3OH-i13:0 | 13.2–18.1 mg |

A. Animal Studies

EXAMPLE 7

Acute Toxicity Test of Q-Can Oral Liquid

Materials and Methods:
Q-can oral liquid; ICR mice weighing 20.5–22.5 g.
Based on the preliminary test which could not determine 50% lethal dose (LD50), twenty ICR mice (half each sex), weighing 20.5–22.5 g in fasting, were given intragastrically with the most endurable capacity of 3 ml Q-can oral liquid per mouse for four times within 24 hours (6 am., 10 am., 4 p.m., and 10 p.m.)

Results:
It was observed that all the tested mice were less active five minutes after every administration, and returned to normal about one hour later. Three mice suffered from diarrhea one or two days after the administration, but none of tested mice died within the following seven days. After the course of treatment, the tested mice were sacrificed and dissected. Visual observation showed no abnormality in internal organs. This limited test indicated that Q-can oral liquid had no toxic effects, even when large doses were taken acutely. Based on the conversion of body surface area, this dose corresponds to 4642 ml Q-can oral liquid per day for an adult weighing 70 kg.

EXAMPLE 8

Subacute Toxicity Test of Q-Can Oral Liquid

Materials and Methods:
Q-can oral liquid: Kunming mice weighing 22–24 g.
Twenty-four mice (half each sex) were randomly divided into a control group and a test group, and were administrated intragastrically with the normal saline in the control group and Q-can oral liquid in the test group at a dosage of 0.8 ml per day for 21 days. On the 22nd day, two mice randomly selected from each group were scarified; the paraffin sections of their viscera were made for microscopic examination.

Results:
No pathologic changes in internal organs were found by either visual observation or observation under microscope. The remaining ten mice in each group were further observed for seven additional days. No mice died in this observation period. This test showed that intragastrical administration of Q-can oral liquid for 21 consecutive days did not result in toxicity or pathologic changes in mice.

EXAMPLE 9

Long-Term Toxicity Test of Q-can Oral Liquid

Material and Methods:
Q-can oral liquid; Forty male and forty female Spraque-Dawley rats weighing 60±0.75 g were supplied by Sino-English Joint Ventured Shanghai Sipure-Bikai Experimental Animal Co. Ltd.

Eighty mice were randomly divided into four groups: a high-dose group (20 ml/kg Q-can oral liquid); a mid-dose group (10 ml/kg Q-can oral liquid); a low-dose group (5 ml/kg Q-can oral liquid) and a control group (10 ml/kg normal saline). The samples were given intragastrically once a day for three months. Over the course of the experiment, behavior, appetite, gastrointestinal reaction and body weight of the rats were recorded. The index of blood routine, blood platelet, electrocardiogram, liver function and renal function were measured. The tested rats were sacrificed and dissected after three-month administration. Visual and pathological examinations were made for their main organs including heart, liver, spleen, lung, kidney, stomach, jejunum and brain.

Results:

Generally speaking, the tested rats were well, no abnormal behavior, no gastrointestinal reaction, good appetite. The curve of weight increase of the test group was similar to the control group (p>0.05). The electrocardiograph examination result was normal. The hematology (including blood routine and blood platelet) was not statistically different between the test group and control group (p>0.05). The liver function (including ALT and TTT) and the renal function (including BUN and Cr) showed no obvious changes either (p>0.05). Although the creatinine of the test group was a bit higher, it was still in the normal range. The pathological section examination of the main organs showed that the cell structure and histomorphology in the test group were not obviously different from those in the control group. It is concluded that Q-can oral liquid can be used safely, based on the fact that continuous administration had no toxicity reactions.

EXAMPLE 10

Effects of Q-can Oral Liquid on Prolonging Life-Span of Fruit Fly Method

Fruit flies of both sexes were divided into control and test groups. In making forage fed to flies, water was used in the control group, while 2%, 10% and 20% concentrations of Q-can Oral liquid were used in the test groups, respectively. The numbers of dead fruit flies were counted every day till the last one died. The mean life-span (mls) and the maximum life-span (MLS) were calculated.

Results:

TABLE 10

Effects on mean and maximum life-span of fruit flies

| group | mls (d, M ± SD) | | MLS (d, M ± SD) | |
| --- | --- | --- | --- | --- |
| | male | female | male | female |
| control | 31.9 ± 9.7 (46) | 26.9 ± 9.6 (47) | 40.0 ± 4.3 [0] | 43.0 ± 4.9 [0] |

TABLE 10-continued

Effects on mean and maximum life-span of fruit flies

| group | mls (d, M ± SD) | | MLS (d, M ± SD) | |
| --- | --- | --- | --- | --- |
| | male | female | male | female |
| Q-can 2% | 30.8 ± 6.5 (45) | 31.8 ± 9.5* (48) | 39.5 ± 2.1 [0] | 63.5 ± 0.7 [1] |
| Q-can 10% | 38.9 ± 13.3* (45) | 35.9 ± 12.4** (47) | 64.5 ± 2.1 [5] | 61.0 ± 4.2 [0] |
| Q-can 20% | 50.8 ± 15.8** (44) | 45.5 ± 14.6** (47) | 64.5 ± 2.1 [12] | 64.5 ± 2.1 [4] |

( ) case number,
[ ] residual number of flies, comparing with control,
*$p < 0.025$,
**$p < 0.001$
Q-can Oral Liquid significantly increased the mean and maximum life-span of fruit flies, suggesting its antiaging function.

EXAMPLE 11

Effects of Q-can Oral Liquid on Hepatic and Cerebral Lipoperoxide Method

Forty Balb/C mice of both sexes were randomly divided into control and three test groups. The mice in the test groups were supplied with Q-can Oral Liquid instead of drinking water for four weeks, and then were starved for 24 hours. The malondiadehyde (MDA) contents were measured to determine the hepatic and cerebral lipoperoxide (LPO) levels.

Results:

TABLE 11

Effect of Q-can on hepatic and cerebral LPO level (MDA nmol/g, X ± SD)

| group | case | male | | female | |
| --- | --- | --- | --- | --- | --- |
| | | liver | brain | liver | brain |
| control | 10 | 75.8 ± 5.50 | 106.8 ± 2.67 | 74.8 ± 4.93 | 108.8 ± 4.10 |
| Q-can 30% | 10 | 56.3 ± 2.20* | 83.0 ± 4.83* | 55.0 ± 3.13* | 87.0 ± 5.13* |
| Q-can 20% | 10 | 63.2 ± 2.30*° | 92.5 ± 3.27*° | 60.8 ± 3.07*° | 94.0 ± 3.39*° |
| Q-can 10% | 10 | 62.2 ± 3.33* | 96.7 ± 3.83* | 61.0 ± 2.27* | 98.8 ± 2.50*° | comparing with control: *$p < 0.001$,
comparing between Q-can 20% and 30%: °$p < 0.01$
Q-can Oral Liquid significantly decreased the hepatic and cerebral LPO levels, suggesting its antiaging function.

EXAMPLE 12

Enhancement of the Effectiveness of Chemotherapeutic Drugs

Materials and Methods:

Q-can oral liquid; mouse liver cancer HAC cell line; male Kunming mice weighing 20–25 g; commercial cyclophosphamide (CP).

Forty mice were randomly divided into 5 groups. In three test groups, 36%, 60% and 100% Q-can oral liquids (diluted with water) were given, respectively, while water was given in both control groups. On the 8th day, 0.2 ml HAC cancer cell suspensions ($10^7$/ml) were injected into the abdominal cavities of each mouse under aseptic condition. On the 1st, 3rd and 5th days after injection. CP (50 mg/kg) was injected i.p. into the mice in all test groups and positive control group. From the 9th day after injection, normal feeding was resumed as before the test. Date of death of each mouse was recorded, and the average life span and the rate of increase in life span were calculated. The rate of increase in life span (ILS %) is defined as following:

$$\frac{\text{Life span of test group} - \text{Life span of control group}}{\text{Life span of control group}} \times 100\%$$

Results:

The results below (Table 12) showed the enhancement of anticancer effect of chemotherapeutic drug, CP, by combining treatment with Q-can oral liquid. The average life span of mice in the control group (without drug) was only 10.63±1.03 days, while that in the positive control group (only taking CP) was 13.06±3.03 days, with ILS of 22.86%. The combination of Q-can oral liquid (with dosage of 60% and 100%) and CP increased the effectiveness of CP, as evidenced by increased average ILS and increased numbers of mice that survived over 17 days (60% prolonged). Therefore the ILS rate by CP treatment has been increased 56.78% and 143.86% by combination with 60% and 100% Q-can oral liquid, respectively. The difference was statistically significant.

(C57/B1 and DBA/2) weighing 18–22 g; Lewis mouse lung tumor.

The mice of the test group were administrated with concentrated Q-can oral liquid at a daily dose of 36 mg specific branched-chain fatty acids per kg weight for 10 days before transplantation of Lewis mouse lung tumor. All the mice were transplanted subcutaneously in the subaxillary region with a piece of Lewis tumor of approximately 2 mm in diameter. The treatments of intraperitoneal injection of chemotherapy drug Cytoxan (CTX) in 30 mg/kg were given once a day after transplantation over an 8 day period for the positive control group. The treatments for the normal control group were daily injection of normal saline for 8 days. The administration of concentrated Q-can oral liquid for the test group was initiated 10 days before tumor transplantation and continued for another 8 days. Finally all the animals were sacrificed by spinal elongation. Tumors were excised and body and tumor weights were recorded.

Results:

The significant inhibition effect of Q-can oral liquid was shown in the test data (Table 13.) Although the inhibition

TABLE 12

Q-can oral liquid enhanced the effectiveness of CP for liver cancer

| group | drug | life span | mice No (>17 d) | prolonged days | ILS % | p* |
|---|---|---|---|---|---|---|
| 1 | — | 10.63 ± 1.03 | 0 | — | — | |
| 2 | 36% Q-can + CP | 12.38 ± 2.37 | 1 | 1.75 ± 2.05 | 16.46 | <0.10 |
| 3 | 60% Q-can + CP | 14.44 ± 3.54 | 2 | 3.94 ± 2.87 | 35.84 | <0.02 |
| 4 | 100% Q-can + CP | 16.56 ± 3.96 | 6 | 5.94 ± 2.96 | 55.75 | <0.01 |
| 5 | CP | 13.06 ± 3.03 | 1 | 2.44 ± 2.58 | 22.86 | <0.05 |

*compared with Group 1 (control group)

EXAMPLE 13

Tumor Inhibition Effects on Mouse Lewis Lung Tumor

Materials and Methods:

Concentrated Q-can oral liquid (containing specific branched-chain fatty acids 3.6 mg/ml); Female F1 mice rate of the positive control group (chemotherapy drug CTX i.p. injection) was higher than the test group, it is noticed that viability of the positive control (70%, only 8-day period) was lower than the test group (100%, 18–28 days), implying toxicity of CTX. As oral administration is expected to be less effective than intraperitoneal injection, change in route of administration or increase in dosage should enhance the tumor inhibitory rate of Q-can oral liquid.

TABLE 13

Effects of Q-can Oral Liquid on Mouse Lewis Lung Carcinoma Xenograft Implanted into Subcutaneous Area of Nude Mice

| group | dose | route | mice No. in./fi. | body weight in./fi. | tumor weight mean ± SD (g) | TIR (%) | p |
|---|---|---|---|---|---|---|---|
| NS | — | i.p. | 12/11 | 21.2/22.5 | 1.90 ± 0.96 | — | |
| CTX | 30 mg/kg | i.p. | 10/7 | 21.2/20.3 | 0.71 ± 0.36 | 62.6 | <0.01 |
| Q-can | 36 mg/kg | i.p. | 10/10 | 20.9/21.9 | 1.11 ± 0.46 | 41.6 | <0.05 |

EXAMPLE 14

Tumor Inhibition Effects on Human Gastric Adenocarcinoma SGC-7901 Xenografted into Nude Mice Material and Methods:

Female Balb/c-nu/nu athymia mice, 6 weeks old, weighing 18–22 g, housed in specific pathogen free (SPF) condition throughout the course of experiment; concentrated Q-can oral liquid contains 3.6 mg/ml specific branched-chain fatty acids; the drug used for positive control mitomycin C (MMC) was commercially available from Kyowa Hakko Kogyo Co., Ltd., Japan.

Human gastric adenocarcinoma SGC-7901 xenograft was established and maintained. For the experiment, the xenograft fragments of diameter of about 2 mm were inoculated subcutaneously into the right submaxillary regions of nude mice. The animals were randomly divided into five groups five days after inoculation. NS and MMC (20 mg/kg) were given once a day i.p. in normal and positive control groups, respectively, while concentrated Q-can oral liquid was given in test groups once a day p.o., starting on the same day, at daily doses of 18, 36 and 72 mg branched-chain fatty acids per kg weight, respectively, for 14 days. Experiment was terminated 20 days post-implantation, and mice were sacrificed by spinal elongation. Tumors were removed and the weights of treated versus control tumors were compared. Inhibition rate was calculated. The experiment was repeated once.

Results:

The results below indicated that Q-can oral liquid at effective doses of 18, 36 and 72 mg/kg given p.o. once a day for 14 days after tumor inoculation offered antitumor activity against human gastric adenocarcinoma SGC-7901 xenograft with no marked toxicity. The tumor inhibition rate increased with dosage of oral administration. The obvious shrinkage of the tumors was observed.

The results from the two tests (Test I and Test II are as follows):

B. Clinical Trials

EXAMPLE 15

Clinical Trial on Effects of Q-can Oral Liquid on Supplementary Treatment of Cancer Methods:

The clinical trial of the effects of Q-can oral liquid as a supplementary treatment of cancer was carried out by the cooperation of five hospitals in China. 333 cases of cancer patients were involved and were randomly divided into two groups, chemotherapy and radiotherapy. The chemotherapy group included a control subgroup, which only took chemotherapy and contained 131 cases, and a test subgroup, which combined chemotherapy with Q-can oral liquid and contained 136 cases. The types of cancer involved included gastric, hepatic, esophageal, colon, pulmonary and mammary cancers, which were distributed similarly and comparably in the two subgroups ($p>0.1$). The radiotherapy group included a control subgroup (radiotherapy only, 32 cases) and a test subgroup (combination of radiotherapy and Q-can oral liquid, 34 cases). The types of cancers involved included nasopharyngeal and laryngeal cancers, which were distributed similarly and comparably in the two subgroups ($p>0.1$). Meanwhile, sex and age distribution of cancer patients in test and control subgroups was comparable ($p>0.1$).

The dosage of Q-can oral liquid for the two test subgroups was 80 ml×2 per day and it was given for two months.

The clinical observations and records were performed daily and filled in the unified observation forms. The changes of the deficiency syndrome, symptoms, blood routine plus platelet counts, the toxic reaction of chemotherapy or radiotherapy, and the side effects of Q-can oral liquid were recorded weekly. The cardiac, hepatic and renal functions, the living quality and the tumor size were examined or analyzed monthly. The serum, albumin and globulin, cellular immune functions (lymphocyte transformation, NK cell and subgroup composition of T-lymphocytes) and the humoral immunity were determined before and after the clinical trials.

TABLE 14

Effects of Q-can oral liquid on human gastric adenocarcinoma xenograft SGC-7901 implanted into subcutaneous areas of nude mice

| Group | dosage | route | schedule | Mice In./Fi. | Body wt. In./Fi. | Tumor wt. X ± SD, g | Inhibition % | p |
|---|---|---|---|---|---|---|---|---|
| Test I | | | | | | | | |
| NS | — | i.p. | Qd × 14 | 12/12 | 21.9/23.3 | 1.17 ± 0.45 | — | |
| MMC | 2.0 mg/kg | i.p. | Qd × 14 | 6/6 | 22.4/22.0 | 0.33 ± 0.24 | 71.49 | <0.01 |
| Q-can | 18 mg/kg | p.o. | Qd × 14 | 6/6 | 22.0/22.5 | 0.80 ± 0.42 | 31.19 | >0.05 |
| Q-can | 36 mg/kg | p.o. | Qd × 14 | 6/6 | 21.9/22.0 | 0.60 ± 0.45 | 48.23 | <0.05 |
| Q-can | 72 mg/kg | p.o. | Qd × 14 | 6/6 | 21.6/21.7 | 0.57 ± 0.35 | 51.28 | <0.05 |
| Test II | | | | | | | | |
| NS | — | i.p. | Qd × 14 | 12/12 | 21.6/23.5 | 1.15 ± 0.30 | — | |
| MMC | 2.0 mg/kg | i.p. | Qd × 14 | 6/6 | 21.1/21.1 | 0.30 ± 0.33 | 73.51 | <0.01 |
| Q-can | 18 mg/kg | p.o. | Qd × 14 | 6/6 | 21.9/22.3 | 0.90 ± 0.59 | 21.58 | >0.05 |
| Q-can | 36 mg/kg | p.o. | Qd × 14 | 6/6 | 22.0/21.6 | 0.66 ± 0.49 | 42.47 | <0.05 |
| Q-can | 72 mg/kg | p.o. | Qd × 14 | 6/6 | 22.3/20.3 | 0.51 ± 0.37 | 55.45 | <0.01 |

Results:

A. Effects on Clinical Symptoms

Four classes of therapeutic effects on deficiency syndrome were defined as:

Significant effect—the symptoms of the deficiency syndrome disappeared or got a significant favorable turn at the end of therapy;

Improvement—the symptoms got a favorable turn at the end of therapy;

Stability—the symptoms remained unchanged;

No effect—the symptoms became worse at the end of therapy.

In the chemotherapy group, the effectiveness rate of the test subgroup was 67.46% (significant effect plus improvement), which was significantly higher than that of the control subgroup (40.60%), p<0.01. In the radiotherapy group, the effectiveness rate of the test subgroup was significantly higher than that of the control subgroup, p<0.05 based on Ridit analysis.

B. Effect on Immune System

TABLE 17

Cellular immunity changes in the chemotherapy group

| item | subgroup | case | Pre-treat (X ± SD)% | Post-treat (X ± SD)% | p |
|---|---|---|---|---|---|
| LTT* | test | 65 | 55.95 ± 8.02 | 56.28 ± 8.55 | <0.01 |
|  | control | 75 | 55.85 ± 8.87 | 49.41 ± 12.21 |  |
| $CD_3$ | test | 30 | 43.53 ± 4.55 | 43.47 ± 5.10 | <0.01 |
|  | control | 30 | 45.47 ± 3.56 | 38.57 ± 4.50 |  |
| $CD_4$ | test | 30 | 45.07 ± 4.60 | 43.10 ± 5.13 | <0.01 |
|  | control | 30 | 42.60 ± 5.20 | 38.27 ± 5.62 |  |
| NK cell | test | 15 | 9.60 ± 5.11 | 12.00 ± 4.23 | <0.01 |
|  | control | 14 | 12.96 ± 4.31 | 10.80 ± 4.00 |  |

*LTT: Lymphocyte Transformation Test

TABLE 18

Humoral immunity changes in the chemotherapy/radiotherapy groups

| Item (g/L) | group | subgroup | case | Pre-treat (X ± SD)% | Post-treat (X ± SD)% | p |
|---|---|---|---|---|---|---|
| IgG | chemotherapy | test | 71 | 10.90 ± 4.69 | 11.92 ± 5.06 | <0.01 |
|  |  | control | 75 | 11.90 ± 4.38 | 11.05 ± 4.99 |  |
| IgA | chemotherapy | test | 72 | 1.63 ± 0.67 | 1.73 ± 1.32 | <0.01 |
|  |  | control | 75 | 1.65 ± 0.76 | 1.38 ± 0.76 |  |
|  | radiotherapy | test | 34 | 1.74 ± 1.31 | 2.39 ± 2.18 | <0.01 |
|  |  | control | 31 | 2.07 ± 1.03 | 1.88 ± 0.80 |  |
| IgM | chemotherapy | test | 71 | 1.24 ± 0.59 | 1.55 ± 1.05 | <0.01 |
|  |  | control | 75 | 1.53 ± 0.78 | 1.30 ± 0.73 |  |

The cellular and humoral immunity was enhanced in the test subgroup of combining chemotherapy and Q-can oral liquid. The concentration of IgA increased in the test subgroup of combining radiotherapy and Q-can oral liquid.

C. Effects on Chemotherapeutic Toxic Reaction

TABLE 15

Symptom changes in the chemotherapy group

| symptom | subgroup | case | mitigation case (%) | stability case (%) | aggravation | p |
|---|---|---|---|---|---|---|
| appetite | Test | 72 | 49(68.06) | 18(25.00) | 5(6.94) | <0.01 |
|  | control | 81 | 18(22.22) | 33(40.74) | 30(37.04) |  |
| weakness | Test | 90 | 56(62.22) | 28(31.11) | 6(16.67) | <0.01 |
|  | control | 70 | 13(13.57) | 29(41.43) | 28(40.00) |  |

TABLE 16

Weight change in the chemotherapy group

| subgroup | case | increase case (%) | stability case (%) | decrease case (%) | p |
|---|---|---|---|---|---|
| test | 136 | 63(46.32) | 33(24.27) | 40(29.41) | <0.01 |
| control | 131 | 20(15.27) | 35(26.72) | 76(58.01) |  |

*increase and decrease were defined as more than 0.5 kg changes of body weight, and intermediate was stability.

TABLE 19

Effects on toxic reaction of blood system

| item | subgroup | case | Pre-treat (X ± SD) | Post-treat (X ± SD) | p |
|---|---|---|---|---|---|
| WBC ($\times 10^9$) | test | 30 | 4.74 ± 1.21 | 5.45 ± 0.86 | <0.01 |
|  | control | 30 | 5.29 ± 0.85 | 4.45 ± 0.80 |  |
| Neutrophil cell | test | 30 | 3.20 ± 0.82 | 3.66 ± 0.69 | <0.01 |
|  | control | 30 | 3.72 ± 0.58 | 3.09 ± 0.45 |  |
| Hb (g/L) | test | 30 | 94.63 ± 18.00 | 96.89 ± 16.08 | <0.01 |
|  | control | 30 | 103.67 ± 13.24 | 99.20 ± 11.63 |  |
| platelet ($\times 10^9$/L) | test | 30 | 140.30 ± 4.88 | 160.03 ± 4.36 | <0.01 |
|  | control | 30 | 157.33 ± 3.52 | 145.53 ± 5.33 |  |

The blood routine and platelet quantity in the test subgroup dropped less than those in the control subgroup. This indicated that Q-can oral liquid can prevent the hemogram decrease caused by chemotherapy. Meanwhile, Q-can oral liquid was effective on the patients whose WBC and Hb were lower than normal before chemotherapy.

TABLE 20

Effects on hepatic function of the chemotherapy group

| | | SGPT (nmol/L, X + SD) | | |
|---|---|---|---|---|
| subgroup | case | pre-treat | post-treat | p |
| test | 89 | 460.06 ± 25.34 | 330.11 ± 245.01 | <0.05 |
| control | 84 | 261.47 ± 191.23 | 284.00 ± 217.30 | |

TABLE 21

Effects on serum protein of chemotherapy

| item | subgroup | case | pre-treat (g/L, X ± SD) | post-treat (g/L, X ± SD) | p |
|---|---|---|---|---|---|
| total protein | test | 101 | 65.31 ± 10.01 | 67.47 ± 5.99 | <0.01 |
| | control | 103 | 65.64 ± 6.53 | 64.20 ± 6.07 | |
| albumin | test | 107 | 38.78 ± 5.65 | 39.13 ± 5.26 | <0.01 |
| | control | 102 | 39.44 ± 4.74 | 38.18 ± 5.24 | |

SGPT decreased and serum total protein increased in the test subgroup of combining chemotherapy and Q-can oral liquid. The results showed that Q-can oral liquid could alleviate the damage of hepatic functions caused by chemotherapy and promote protein synthesis, thus protecting the liver.

TABLE 22

Effects on renal functions of the chemotherapy group

| | | Blood urea nitrogen (nmol/L) | | | Blood creatine (nmol/L) | | |
|---|---|---|---|---|---|---|---|
| subgroup | case | Pre-treat | post-treat | case | Pre-treat | Post-treat | p |
| test | 111 | 5.13 ± 2.95 | 4.95 ± 1.33 | 110 | 97.15 ± 30.64 | 97.99 ± 23.46 | <0.01 |
| control | 100 | 4.26 ± 1.03 | 5.04 ± 1.42 | 90 | 89.28 ± 22.13 | 107.08 ± 41.27 | |

Blood urea nitrogen and creatine decreased in the test group, which indicated that Q-can oral liquid could alleviate the damage of renal function caused by chemotherapy.

In summary, compared with the chemotherapy only treatment of 131 cases of cancer patients, the results of combinational treatment with Q-can oral liquid showed markedly enhanced therapeutical effects with statistical significance. These effects included amelioration of the deficiency syndrome, improvement of the appetite, weakness, living quality and immune functions, mitigation of the degree of leucopenic action induced by chemotherapy, alleviation of the low leukocyte count and the hemoglobin concentration which decreased after treatment, and protection of the hepatic and the renal functions. In comparison with the radiotherapy only treatment, the amelioration of the deficiency syndrome and increase of the serum IgG level were found in cancer patients, who were treated by combination of radiotherapy with Q-can oral liquid. Q-can oral liquid had no toxic effects on the blood, heart, liver and kidney. Thus, Q-can oral liquid can be used as a supplementary therapeutic agent for cancer patients.

EXAMPLE 16

Clinical Observation for 35 Cases of American Prostate Cancer Patients Treated by Q-can Oral Liquid The effect of Q-can oral liquid on PSA levels was tested for 8–18 weeks (average 14 weeks) in two hospitals in the USA, where an integrative approach to treating prostate cancer was applied. Patients were not on radiotherapy, chemotherapy, or hormonal treatment during the recording period and followed a customized nutritional protocol. At a daily dosage of 250 ml concentrated Q-can oral liquid (containing 300 mg specific branched-chain fatty acids), assay of PSA level was made for all patients. The average drop in PSA level was noted. It is also found that drops in PSA level of the patients who had higher pre-treat PSA level was more significant than those of the patients who had lower pre-treat PSA level.

TABLE 23

The effects of Q-can oral liquid on PSA level (mg/ml)

| Case Number | Pre-treat (mean ± SD) | Post-treat (mean ± SD) | p |
|---|---|---|---|
| 35 | 10.2 ± 10.72 | 7.45 ± 6.06 | <0.01 |

EXAMPLE 17

Effects of Iso-C15 on Psoriasis Skin Disease 13-methyltetradecanoic acid (iso-C15) was prepared by dissolving in NaOH solution and then in 0.8% Tween 80 with pH 7.5, with resulting concentration 10%. The iso-C15 cream was prepared with liposome technology.

Three psoriases patients topically applied iso-C15 cream on skin lesions three times per day for one month. The symptoms were obviously relieved (itching, flaking and red patches), and psoriases spots disappeared in one patient and 50% area reduced in the other two.

EXAMPLE 18

Industrial Process for Making Fermentation Liquid

This example describes one method of industrial production of Q-can oral liquid in a more detailed manner.

Medium composition is: soybean 40 kg (milling to milk and removing residue), $K_2HPO_4$ 200 mg, $CaCO_3$ 200 g, yeast extract 160 g, $MgSO_4$ 80 g, NaCl 80 g, $Na_2MoO_4$ 10 ppm. ZnSO₄ 10 ppm, CoCl₂ 5 ppm, NaHNO₃ 2 ppm, soybean oil (as antifoam addition) 4 kg, and add water to 400 kg totally.

The above media is put into a seeding tank and lead steam 120° C. for 30 minutes, then cooled to 30° C. Onto the seeding tank are inoculated 3 kg liquid cultures, which were cultured on the incubator shaker at 30° C. for 24 hours. Fermentation proceeds in the seeding tank for 24 hours, 30° C. temperature, 200 rpm agitation speed, and 1:1 (v/v min) aeration rate. After confirming no infection under microscope, it is then transferred into a 10 ton production fermenter for 48 hours, where compared to that in the seeding tank before, the media is ten times in quantity and the same percentage of the composition, and the same parameters of temperature, agitation speed and aeration rate are used. When fermentation is finished and no infection is confirmed under microscope, the temperature is increased to 100° C. to autoclave for 30 minutes. The cooled solution can be packaged and the packaged fermented solution is again autoclaved at 118° C. for 45 minutes. This is a semi-finished product waiting for quality inspection and final package as the Q-can oral liquid product.

Every description in the above specification of a numerical range and of a genus is intended to inherently include a description of all possible values and subranges within the range, and all possible species and subgenuses within the genus, respectively.

The disclosures of U.S. application Ser. No. 09/173,681 filed Oct. 16, 1998, and of Provisional Patent Application No. 60/081,712, filed Apr. 14, 1998, are hereby incorporated by reference.

The invention claimed is:

1. A method of making a terminally methyl-branched iso- or anteiso-fatty acid, or a mixture of said fatty acids, which comprises culturing a bacteria strain containing said fatty acid(s) to form a fermentation solution containing said fatty acid(s), and then isolating said fatty acid(s), from the fermentation solution, wherein the bacteria strain is from the genus *Stenotrophomonas*.

2. The method of claim 1, wherein the culture medium comprises a soybean medium.

3. The method of claim 2, wherein the soybean medium has the following formula:

| | |
|---|---|
| Soybean | 5–10% |
| or soybean milk or bean cake (by soybean wt.) | 5–15% |
| Yeast extract | 0.02–0.5% |
| or yeast powder | 0.02–0.5% |
| CaCO₃ | 0.05–0.25% |
| K₂HPO₄ | 0.02–0.10% |
| MgSO₄ | 0.01–0.05% |
| NaCl | 0.01–0.04% |
| Na₂MoO₄ | 5.0–30 ppm |
| ZnSO₄ | 2.5–15 ppm |
| CoCl₂ | 5.0–20 ppm. |

4. The method of claim 1, wherein the bacterial strain is *Stenotrophomonas maltophilia*.

5. The method of claim 4, wherein said bacterial strain is assigned ATCC 202105.

6. A method of making a fermentation solution containing at least one terminally methyl-branched iso- or anteiso-fatty acid, which comprises culturing a bacteria strain containing said fatty acid in a nutritive medium to form a fermentation solution containing said fatty acid, wherein the bacteria strain is from the genus *Stenotrophomonas*.

7. The method of claim 6, wherein the nutritive medium comprises a soybean medium.

8. The method of claim 7, wherein the soybean medium has the following formula:

| | |
|---|---|
| Soybean | 5–10% |
| or soybean milk or bean cake (by soybean wt.) | 5–15% |
| Yeast extract | 0.02–0.5% |
| or yeast powder | 0.02–0.5% |
| CaCO₃ | 0.05–0.25% |
| K₂HPO₄ | 0.02–0.10% |
| MgSO₄ | 0.01–0.05% |
| NaCl | 0.01–0.04% |
| Na₂MoO₄ | 5.0–30 ppm |
| ZnSO₄ | 2.5–15 ppm |
| CoCl₂ | 5.0–20 ppm. |

9. The method of claim 6, wherein the bacterial strain is *Stenotrophomonas maltophilia*.

10. The method of claim 9, wherein said bacterial strain is assigned ATCC 202105.

11. A product made by the method of claim 6.

12. A product made by the method of claim 7.

13. A product made by the method of claim 8.

14. A product made by the method of claim 9.

15. A product made by the method of claim 10.

16. The product of claim 11, which is in the form of a liquid, powder, capsule, tablet, injection, or encapsulated with liposome, or topically applied in the form of a cream, ointment, or lotion.

17. The product of claim 12, which is in the form of a liquid, powder, capsule, tablet, injection, or encapsulated with liposome, or topically applied in the form of a cream, ointment, or lotion.

18. The product of claim 13, which is in the form of a liquid, powder, capsule, tablet, injection, or encapsulated with liposome, or topically applied in the form of a cream, ointment, or lotion.

19. The product of claim 14, which is in the form of a liquid, powder, capsule, tablet, injection, or encapsulated with liposome, or topically applied in the form of a cream, ointment, or lotion.

20. The product of claim 15, which is in the form of a liquid, powder, capsule, tablet, injection, or encapsulated with liposome, or topically applied in the form of a cream, ointment, or lotion.

* * * * *